United States Patent
Lin et al.

(10) Patent No.: US 8,110,630 B2
(45) Date of Patent: *Feb. 7, 2012

(54) SILICONE ELASTOMER GELS

(75) Inventors: Shaow Lin, Midland, MI (US); James McVie, Midland, MI (US); Paul Vandort, Sanford, MI (US)

(73) Assignee: Dow Corning Corporation, Midland, MI (US)

( * ) Notice: Subject to any disclaimer, the term of this patent is extended or adjusted under 35 U.S.C. 154(b) by 577 days.

This patent is subject to a terminal disclaimer.

(21) Appl. No.: 12/293,571

(22) PCT Filed: Mar. 20, 2007

(86) PCT No.: PCT/US2007/006894
§ 371 (c)(1),
(2), (4) Date: Sep. 19, 2008

(87) PCT Pub. No.: WO2007/109260
PCT Pub. Date: Sep. 27, 2007

(65) Prior Publication Data
US 2010/0172849 A1     Jul. 8, 2010

Related U.S. Application Data

(60) Provisional application No. 60/784,340, filed on Mar. 21, 2006, provisional application No. 60/838,803, filed on Aug. 18, 2006.

(51) Int. Cl.
*A61K 8/89* (2006.01)

(52) U.S. Cl. ........ 524/588; 524/261; 524/267; 524/315; 525/477; 525/479; 528/31; 528/32; 528/37; 424/486

(58) Field of Classification Search .......... None
See application file for complete search history.

(56) References Cited

U.S. PATENT DOCUMENTS

| | | |
|---|---|---|
| 3,159,601 A | 12/1964 | Ashby |
| 3,220,972 A | 11/1965 | Lamoreaux |
| 3,296,291 A | 1/1967 | Chalk |
| 3,419,593 A | 12/1968 | Willing |
| 3,516,946 A | 6/1970 | Modic |
| 3,814,730 A | 6/1974 | Karstedt |
| 3,928,629 A | 12/1975 | Chandra et al. |
| 3,989,668 A | 11/1976 | Lee et al. |
| 4,122,029 A | 10/1978 | Gee et al. |
| 4,987,169 A | 1/1991 | Kuwata et al. |
| 5,036,117 A | 7/1991 | Chung et al. |
| 5,175,325 A | 12/1992 | Brown et al. |
| 5,236,986 A | 8/1993 | Sakuta |
| 5,380,527 A | 1/1995 | Legrow et al. |
| 5,387,417 A | 2/1995 | Rentsch |
| 5,412,004 A | 5/1995 | Tachibana et al. |
| 5,493,041 A | 2/1996 | Biggs et al. |
| 5,654,362 A | 8/1997 | Schulz, Jr. et al. |
| 5,760,116 A | 6/1998 | Kilgour et al. |
| 5,811,487 A | 9/1998 | Schulz, Jr. et al. |
| 5,869,727 A | 2/1999 | Crane et al. |
| 5,880,210 A | 3/1999 | Schulz, Jr. et al. |
| 5,889,108 A | 3/1999 | Zhang |
| 5,919,441 A | 7/1999 | Mendolia et al. |
| 5,929,162 A | 7/1999 | Horne et al. |
| 5,929,164 A | 7/1999 | Zhang |
| 5,981,680 A | 11/1999 | Petroff et al. |
| 5,998,542 A | 12/1999 | Horne et al. |
| 6,013,682 A | 1/2000 | Dalle et al. |
| 6,051,216 A | 4/2000 | Barr et al. |
| 6,200,581 B1 | 3/2001 | Lin et al. |
| 6,207,717 B1 | 3/2001 | Lin et al. |
| 6,262,170 B1 | 7/2001 | Kilgour et al. |
| 6,271,295 B1 | 8/2001 | Powell et al. |
| 6,291,563 B1 | 9/2001 | Horne et al. |
| 6,331,604 B1 | 12/2001 | Wang et al. |
| 6,365,670 B1 | 4/2002 | Fry |
| 6,531,540 B1 | 3/2003 | O'Brien |
| 6,605,734 B2 | 8/2003 | Roy et al. |
| 7,078,026 B2 | 7/2006 | Ferrari et al. |
| 2001/0041771 A1 | 11/2001 | Kondo et al. |
| 2003/0072730 A1 | 4/2003 | Tournilhac |
| 2003/0170188 A1 | 9/2003 | Ferrari et al. |
| 2003/0235553 A1 | 12/2003 | Lu et al. |
| 2004/0091440 A1 | 5/2004 | Kamei et al. |
| 2004/0092655 A1 | 5/2004 | Otomo |
| 2004/0180032 A1 | 9/2004 | Manelski et al. |
| 2004/0228821 A1 | 11/2004 | Sunkel et al. |
| 2009/0317343 A1 | 12/2009 | Lin et al. |
| 2010/0172849 A1 | 7/2010 | Shaow et al. |
| 2010/0183525 A1 | 7/2010 | Lin |

FOREIGN PATENT DOCUMENTS

| | | |
|---|---|---|
| EP | 0922734 | 6/1999 |
| EP | 1148099 | 10/2001 |
| WO | 03093349 | 11/2003 |
| WO | 2004084844 | 10/2004 |
| WO | 2005100444 | 10/2005 |
| WO | 2009042535 | 4/2009 |

OTHER PUBLICATIONS

"Synthesis of New Organic Crosslinking Reagents Containing SiH Bonds and Curing System Thereof" authored by Iwahara et al. and published in Polymer Journal (1993) 25 (4), 379-389.* Abstract and machine translation for JP 6-49347 (Feb. 1994).*

* cited by examiner

*Primary Examiner* — Marc Zimmer
(74) *Attorney, Agent, or Firm* — Alan Zombeck

(57) ABSTRACT

Gel compositions containing a silicone elastomer from the reaction of an organohydrogensiloxane having at least two SiH containing cyclosiloxane rings in its molecule, a compound having at least two aliphatic unsaturated hydrocarbon groups in its molecule, and a hydrosilylation catalyst. The silicone elastomer reaction product may itself be a gelled composition, or optionally may be contained in a carrier fluid to form a gel. The gel compositions may further contain a personal or healthcare active. The actives may be incorporated into the gel via either a pre or post load method.

19 Claims, 1 Drawing Sheet

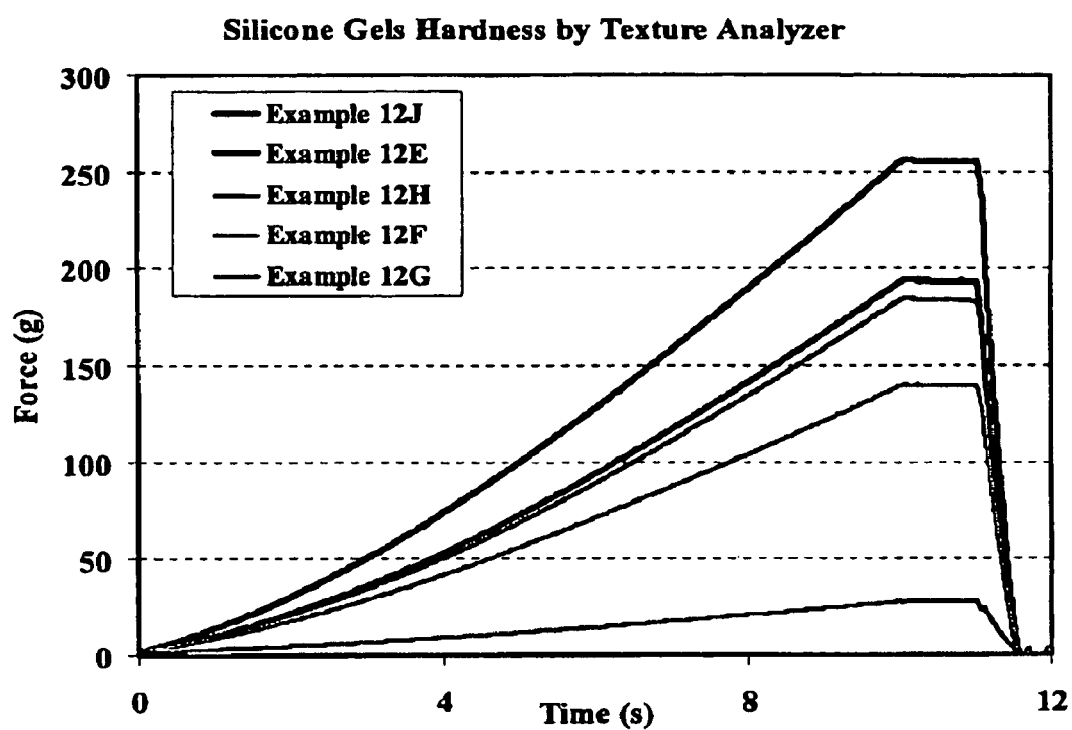
Figure 1. The compression force as function of probe penetration time into gels, as registered by the Texture Analyzer

SILICONE ELASTOMER GELS

CROSS REFERENCE TO RELATED APPLICATIONS

This application is a U.S. national stage filing under 35 U.S.C. §371 of PCT Application No. PCT/US07/006894 filed on Mar. 20, 2007, currently pending, which claims the benefit of U.S. patent application Ser. No. 60/784,340 filed on 21 Mar. 2006, and U.S. patent application Ser. No. 60/838,803, filed on 18 Aug. 2006, under 35 U.S.C. §119(e), which are hereby incorporated by reference.

TECHNICAL FIELD

This invention relates to gel compositions containing a silicone elastomer from the reaction of an organohydrogensiloxane having at least two SiH containing cyclosiloxane rings in its molecule, a compound, or mixture of compounds having at least two aliphatic unsaturated hydrocarbon groups in its molecule, and a hydrosilylation catalyst. The silicone elastomer reaction product may itself be a gelled composition, or optionally may be contained in a carrier fluid to form a gel. The gel compositions may further contain a personal or healthcare active. The actives may be incorporated into the gel via either a pre or post load method.

BACKGROUND

Silicone elastomers have been used extensively in personal care applications for their unique silky and powdery sensory profile. Most of these elastomers can gel volatile silicones fluids as well as low polarity organic solvents such as isododecane. Representative examples of such silicone elastomers are taught in U.S. Pat. Nos. 5,880,210, and 5,760,116. To improve compatibilities of silicone elastomers with various personal care ingredients, alkyls, polyether, amines or other organofunctional groups have been grafted onto the silicone elastomer backbone. Representative of such organofunctional silicone elastomers are taught in U.S. Pat. Nos. 5,811,487, 5,880,210, 6,200,581, 5,236,986, 6,331,604, 6,262,170, 6,531,540, and 6,365,670. Many of these silicone elastomers have limited compatibilities with various personal care ingredients, personal care actives and healthcare actives. These elastomers loose thickening and gelling efficiency, and even sensory benefits in the presence of personal care ingredients, personal care actives and healthcare actives. There is a need to further improve compatibilities of silicone elastomers with various personal care ingredients and actives.

However, there is still a need to further improve the efficiency of gelling volatile cosmetic fluids such as volatile silicones by silicone elastomers, and in particular to improve the rheological thickening effects by the addition of silicone elastomers to volatile cosmetic fluids. Furthermore, additional benefits are also sought for gelled compositions, such as improving the clarity of gelled silicone compositions and/or improved aesthetics upon application on skin.

The present inventors have discovered that silicone elastomers derived from cyclic organohydrogensiloxanes provide gelled compositions efficiently. The resulting gelled compositions also possess additional benefits, such as improved aesthetics and improved compatibilities with personal care ingredients and actives.

SUMMARY

This disclosure relates to a gel composition comprising a silicone elastomer from the reaction of;

A) an organohydrogensiloxane having at least two SiH containing cyclosiloxane rings in its molecule
B) a compound or mixture of compounds having at least two aliphatic unsaturated hydrocarbon groups in its molecule,
C) a hydrosilylation catalyst, and;
D) an optional earner fluid.

This disclosure further relates to a process for preparing a silicone elastomer gel containing an active comprising:
I) reacting;
a) an organohydrogencyclosiloxane having at least two SiH units on a siloxane ring,
B) a compound or mixture of compounds having at least two aliphatic unsaturated hydrocarbon groups in its molecule,
C) a hydrosilylation catalyst, to form
A) an organohydrogensiloxane having at least two SiH containing cyclosiloxane rings in its molecule,
wherein the molar ratio of the SiH units of component a) to the aliphatic unsaturated groups of component B) ranges from 2/1 to 8/1,
II) further reacting;
A) the organohydrogensiloxane having at least two SiH containing cyclosiloxane rings in its molecule, with additional quantities of
B) the compound or mixture of compounds containing at least two aliphatic unsaturated groups in its molecules,
C) the hydrosilylation catalyst, in the presence of
D) an optional carrier fluid, and
E) a personal care or healthcare active, to form the silicone elastomer gel.

A personal care or healthcare active may be incorporated into the silicone organic elastomer gel by having it be present during the formation of the silicone organic elastomer gel (pre-load method) or admixing it with a formed silicone organic elastomer gel (post-load method).

DETAILED DESCRIPTION (A) The Organohydrogensiloxane Having at Least Two SiH Containing Cyclosiloxane Rings Component (A) in the present invention is an organohydrogensiloxane having at least two SiH containing cyclosiloxane rings in its molecule. Organohydrogensiloxanes suitable as component A) in the present invention are any organopolysiloxanes having in its molecule at least two cyclosiloxane rings with at least one silicon bonded hydrogen (SiH) unit on each siloxane ring. Organopolysiloxanes are well known in the art and are often designated as comprising any number of ($R_3SiO_{0.5}$), ($R_2SiO$), ($RSiO_{1.5}$), or ($SiO_2$) siloxy units where R is independently any organic group. When R is methyl in the siloxy unit formulas of an organopolysiloxane, the respective siloxy units are often designated as M, D, T or Q siloxy units. Cyclosiloxane rings contain at least three siloxy units (that is the minimum needed in order to form a siloxane ring), and may be any combination of ($R_3SiO_{0.5}$), ($R_2SiO$), ($RSiO_{1.5}$), or ($SiO_2$) siloxy units that forms a cyclic structure, providing at least one of the cyclic siloxy units on each siloxane ring contains one SiH unit, that is there is at least one ($R_2HSiO_{0.5}$), ($RHSiO$), or a ($HSiO_{1.5}$) siloxy unit present in the ring. These siloxy units can be represented as $M^H$, $D^H$, and $T^H$ siloxy units respectively when R is methyl.

The cyclosiloxane rings of A) the organohydrogensiloxane are linked together by a divalent organic or siloxane group, or combination thereof. The divalent linking group may be designated as Y and the cyclosiloxane as G. Thus, the organohydrogensiloxane of the present invention may be represented by the general formula G-[Y-G]$_\alpha$, where G is a cyclosiloxane as described above and Y is a divalent organic, a siloxane, a polyoxyalkylene group, or combination thereof, and the subscript α is greater than zero.

When Y is a divalent organic, it may be a divalent hydrocarbon containing 1 to 30 carbons, either as aliphatic or aromatic structures, and may be branched or un-branched. Alternatively, Y can be an alkylene group containing 2 to 20 carbons, or alternatively containing 4 to 12 carbons.

When Y is a divalent organic, it may also be selected from an organic polymer, such as a polyoxyalkylene group.

When Y is a siloxane group it may be selected from any organopolysiloxane containing at least two divalent hydrocarbon groups, designated as $R^1$. Thus, the siloxane linking group can be any organopolysiloxane comprising at least two siloxane units represented by the average formula $R^1R_mSiO_{(4-m)/2}$
wherein
R is an organic group,
$R^1$ is a divalent hydrocarbon, and
m is zero to 3

The $R^1$ group may be present on any mono, di, or tri-siloxy unit in an organopolysiloxane molecule, for example; $(R^1R_2SiO_{0.5})$, $(R^1RSiO)$, or $(R^1SiO_{1.5})$, as well as in combination with other siloxy units not containing an $R^1$ substituent, such as $(R_3SiO_{0.5})$, $(R_2SiO)$, $(RSiO_{1.5})$, or $(SiO_2)$ siloxy units where R is independently any organic group providing there are at least two $R^1$ substituents in the organopolysiloxane. Representative $R^1$ groups include; ethylene, propylene, butylene, isobutylene, hexylene, and similar homologs. Alternatively, $R^1$ is ethylene.

Representative, non-limiting, examples of such siloxane based structures suitable as siloxane linking groups include;

$(R_2R^1SiO_{0.5})(R_2SiO)_x(R_2R^1SiO_{0.5})$

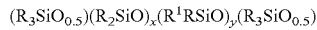

$(R_3SiO_{0.5})(R_2SiO)_x(R^1RSiO)_y(R_3SiO_{0.5})$

$(R_3SiO_{0.5})(R_2SiO)_x(R^1RSiO)_y(RSiO_{1.5})_z(R_3SiO_{0.5})$ where $x \geq 0$, $y \geq 2$, and z is $\geq 0$ Organohydrogensiloxane having at least two SiH containing cyclosiloxane rings (component A) may be prepared via a hydrosilylation reaction of
a) an organohydrogencyclosiloxane having at least two SiH units on the siloxane ring and,
B) a compound or mixture of compounds having at least two aliphatic unsaturated groups in its molecule.

The organohydrogencyclosiloxane (a) having at least two SiH units on the siloxane ring may contain any number of siloxy units (as defined above) provided there are at least two SiH units on the cyclosiloxane ring. For example, the cyclic siloxane can comprise any number of M, $M^H$, D, $D^H$, or $T^H$ siloxy units. Representative, non-limiting examples of such organohydrogencyclosiloxanes useful to prepare component (A) have the average formula $D^H_aD_b$ where a is $\geq 1$ and b is $\geq 0$, and a+b $\geq 3$. Alternatively, the organohydrogencyclosiloxane may be selected from those having the formula $[(CH_3)HSiO]_g$ where g is 3-8, such as $D^H_4$, $D^H_5$, $D^H_6$, or mixtures thereof.

Suitable compounds containing at least two aliphatic unsaturated hydrocarbon groups in its molecule are described below as component B).

Hydrosilylation reactions involving organohydrogensiloxanes and unsaturated compounds are well known. Any suitable hydrosilylation catalysts know in the art may be used, or alternatively may be selected from those described below as component C). Any of the known hydrosilylation techniques and reactions may be employed to prepare component A) from i) organohydrogencyclosiloxane having at least two SiH units on the siloxane ring and, B) a compound or mixture of compounds having at least two aliphatic unsaturated groups in its molecule. However, the reaction is conducted in such a manner to provide an organohydrogensiloxane having at least two SiH containing cyclosiloxane rings in its molecule.

Thus, component A of the present invention contains at least two silicon-bonded hydrogen atom per molecule, alternatively at least 4 silicon-bonded hydrogen atoms per molecule, or alternatively at least 6 silicon-bonded hydrogen atoms per molecule. This can be accomplished by using in the hydrosilylation reaction a molar excess of the a) the organohydrogencyclosiloxane having at least two SiH units on the siloxane ring vs. the compound containing at least two aliphatic unsaturated groups in its molecule. The molar excess may be expressed as the molar ratio of SiH units to unsaturated group, such ratio may range from 2/1 to 8/1, alternatively from 2/1 to 6/1, or alternatively from 3/1 to 4/1.

Alternatively, the organohydrogensiloxane useful as component A) may be selected from any of the organohydrogensiloxanes taught in WO03/093349, which is herein incorporated by reference for its teaching of suitable organohydrogensiloxanes.

The organohydrogensiloxane useful as component A) in the present invention typically have a viscosity from 5 to 50,000 mPa·s, alternatively from 10 to 10,000 mPa·s, or alternatively from 25 to 2,000 mPa·s.

Additives known as inhibitors or stabilizers may be added to component A). Inhibitors such as those described in WO03/093369 may be added for the purpose of stabilizing component A) during storage, or prior to the addition of component B) to prepare the silicone elastomer gel. The inhibitor may be selected from any compound known to have inhibiting effects of platinum based hydrosilylation reactions. Examples of known inhibitors include triphenyl phosphate, tocopherol (vitamin E), and butylated hydroxy toluene. A particularly preferred inhibitor is vitamin A palmitate, or VAP. When VAP is used, it is typically added at 0.05 to 2.0 parts per 100 parts of component A).

(B) The Compound or Mixture of Compounds Having at Least Two Aliphatic Unsaturated Hydrocarbon Groups in its Molecule Component (B) is a compound, or any mixture of compounds, containing at least two aliphatic unsaturated groups in its molecule. The compound may be any diene, diyne or ene-yne compound. Diene, diyne or ene-yne compounds are those compounds (including polymeric compounds) wherein there are at least two aliphatic unsaturated groups with some separation between the groups within the molecule. Typically, the unsaturation groups are at the termini of the compound, or pendant if part of a polymeric compound. Compounds containing terminal or pendant unsaturated groups can be represented by the formula $R^2$—Y—$R^2$ where $R^2$ is a monovalent unsaturated aliphatic hydrocarbon group containing 2 to 12 carbon atoms, and Y is a divalent organic or siloxane group or a combination of these. Typically $R^2$ is $CH_2$=CH—, $CH_2$=CHCH$_2$—, $CH_2$=CH(CH$_2$)$_4$—, $CH_2$=C(CH$_3$)CH$_2$— or CH≡C—, and similar substituted unsaturated groups such as $H_2C$=C(CH$_3$)—, and HC≡C(CH$_3$)—.

The compound having the formula $R^2$—Y—$R^2$ as component B) may be considered as being a "organic", "hydrocarbon", "organic polymer", "polyether" or "siloxane", or combinations thereof, depending on the selection of Y. Y may be a divalent hydrocarbon, a siloxane, a polyoxyalkylene, a polyalkylene, a polyisoalkylene, a hydrocarbon-silicone copolymer, or mixtures thereof.

In one embodiment, the component (B) is selected from an organic compound, herein denoted as ($B^1$), having the formula $R^2$—$Y^1$—$R^2$ where $R^2$ is a monovalent unsaturated aliphatic group containing 2 to 12 carbon atoms and $Y^1$ is a divalent hydrocarbon. The divalent hydrocarbon $Y^1$ may contain 1 to 30 carbons, either as aliphatic or aromatic structures, and may be branched or un-branched. Alternatively, the linking group $Y^1$ in $B^1$ may be an alkylene group containing 1 to 12 carbons. Component ($B^1$) may be selected from α,ω-unsaturated alkenes or alkynes containing 1 to 30 carbons, and mixtures thereof. Component ($B^1$) may be exemplified by, but not limited to 1,4-pentadiene, 1,5-hexadiene; 1,6-heptadiene; 1,7-octadiene, 1,8-nonadiene, 1,9-decadiene, 1,11-dodecadiene, 1,13-tetradecadiene, and 1,19-eicosadiene, 1,3-butadiyne, 1,5-hexadiyne (dipropargyl), and 1-hexene-5-yne.

In another embodiment, the component (B) is selected from a $R^2$—$Y^2$—$R^2$ compound where $Y^2$ is a siloxane, herein denoted as ($B^2$). The $Y^2$ siloxane group may be selected from any organopolysiloxane bonded to at least two organic groups having aliphatic unsaturation, designated as $R^2$, to form $R^2$—$Y^2$—$R^2$ structures. Thus, component ($B^2$) can be any organopolysiloxane, and mixtures thereof, comprising at least two siloxane units represented by the average formula $R^2R_mSiO_{(4-m)/2}$
wherein
R is an organic group,
$R^2$ is a monovalent unsaturated aliphatic group as defined above, and
m is zero to 3

The $R^2$ group may be present on any mono, di, or tri siloxy unit in an organopolysiloxane molecule, for example; ($R^2R_2SiO_{0.5}$), ($R^2RSiO$), or ($R^2SiO_{1.5}$); as well as in combination with other siloxy units not containing an $R^2$ substituent, such as ($R_3SiO_{0.5}$), ($R_2SiO$), ($RSiO_{1.5}$), or ($SiO_2$) siloxy units where R is independently any organic group, alternatively a hydrocarbon containing 1 to 30 carbons, alternatively an alkyl group containing 1 to 30 carbons, or alternatively methyl; providing there are at least two $R^2$ substituents in the organopolysiloxane.

Representative, non-limiting, examples of such siloxane based $R^2$—$Y^2$—$R^2$ structures suitable as component ($B^2$) include;
($R_2R^2SiO_{0.5}$)($SiO_2$)$_w$($R_2R^2SiO_{0.5}$)
($R_2R^2SiO_{0.5}$)($SiO_2$)$_w$($R_2SiO$)$_x$($R_2R^2SiO_{0.5}$)
($R_2R^2SiO_{0.5}$)($R_2SiO$)$_x$($R_2R^2SiO_{0.5}$)
($R_3SiO_{0.5}$)($R_2SiO$)$_x$($R^2RSiO$)$_y$($R_3Si^O_{0.5}$)
($R_3SiO_{0.5}$)($R_2SiO$)$_x$($R^2RSiO$)$_y$($RSiO_{1.5}$)$_z$($R_3SiO_{0.5}$)
($R_3SiO_{0.5}$)($R_2SiO$)$_x$($R_2SiO$)$_y$($SiO_2$)$_w$($R_3SiO_{0.5}$)
where $w≧0$, $x≧0$, $y≧2$, and z is $≧0$, R is an organic group, and
$R^2$ is a monovalent unsaturated aliphatic hydrocarbon group.

$B^2$ may be selected from vinyl functional polydimethylsiloxanes (vinyl siloxanes) or hexenyl functional polydimethylsiloxanes (hexenyl siloxanes), such as those having the average formula;

$CH_2$=$CH(Me)_2SiO[Me_2SiO]_xSi(Me)_2CH$=$H_2$ $CH_2$=$CH$—$(CH_2)_4$-$(Me)_2SiO[Me_2SiO]_xSi(Me)_2$-$(CH_2)_4$—$CH$=$CH_2$ $Me_3SiO[(Me)_2SiO]_x[CH_2$=$CH(Me)SiO]_ySiMe_3$ wherein Me is methyl,
$x≧0$, alternatively x is 0 to 200, alternatively x is 10 to 150,
$y≧2$, alternatively y is 2 to 50, alternatively y is 2 to 10.

Vinyl functional polydimethylsiloxanes are known, and there are many commercially available.

In another embodiment, component (B) is selected from a polyether compound, herein denoted as ($B^3$), having the formula $R^2$—$Y^3$—$R^2$ compound where $R^2$ is as defined above and $Y^3$ is a polyoxyalkylene group having the formula $(C_nH_{2n}O)_b$, wherein n is from 2 to 4 inclusive,
b is greater than 2,
alternatively b can range from 2 to 200,
or alternatively b can range from 2 to 100.

The polyoxyalkylene group typically can comprise oxyethylene units ($C_2H_4O$), oxypropylene units ($C_3H_6O$), oxybutylene or oxytetramethylene units ($C_4H_8O$), or mixtures thereof. Thus, the $R^2$—$Y^3$—$R^2$ compound may be selected from a polyoxyalkylene group having the formula $R^2$—$[(C_2H_4O)_c(C_3H_6O)_d(C_4H_8O)_e]$—$R^2$ where c, d, and e may each independently range from 0 to 200, providing the sum of c+d+e is greater than 2, alternatively the sum of c+d+e ranges from 2 to 200, or alternatively the sum of c+d+e ranges from 2 to 100.

Alternatively, the polyoxyalkylene group comprises only oxypropylene units $(C_3H_6O)_d$. Representative, non-limiting examples of polyoxypropylene containing $R^2$—$Y^3$—$R^2$ compounds include;
$H_2C$=$CHCH_2[C_3H_6O]_dCH_2CH$=$CH_2$
$H_2C$=$CH[C_3H_6O]_dCH$=$CH_2$
$H_2C$=$C(CH_3)CH_2[C_3H_6O]_dCH_2C(CH_3)$=$CH_2$
$HC$≡$CCH_2[C_3H_6O]_dCH_2C$≡$CH$
$HC$≡$CC(CH_3)_2[C_3H_6O]_dC(CH_3)_2C$≡$CH$
where d is as defined above.

Representative, non-limiting examples of polyoxybutylene or poly(oxytetramethylene) containing $R^2$—$Y^3$—$R^2$ compounds include;
$H_2C$=$CHCH_2[C_4H_8O]_eCH_2CH$=$CH_2$
$H_2C$=$CH[C_4H_8O]_eCH$=$CH_2$
$H_2C$=$C(CH_3)CH_2[C_4H_8O]_eCH_2C(CH_3)$=$CH_2$
$HC$≡$CCH_2[C_4H_8O]_eCH_2C$≡$CH$
$HC$≡$CC(CH_3)_2[C_4H_8O]_eC(CH_3)_2C$≡$CH$ Component B) may also be a mixture of various polyethers, i.e. a mixture of $B^3$ components.

In another embodiment, component (B) is selected from a $R^2$—$Y^4$—$R^2$ compound, herein denoted as ($B^4$), where $R^2$ is as defined above and $Y^4$ is a polyalkylene group, selected from C2 to C6 alkylene units or their isomers. One example is polyisobutylene group which is a polymer containing isobutylene unit. The molecular weight of the polyisobutylene group may vary, but typically ranges from 100 to 10,000 g/mole. Representative, non-limiting examples of $R^2$—Y—$R^2$ compounds containing a polyisobutylene group includes those obtained from BASF under the tradename of OPPONOL BV, such as OPPONOL BV 5K, a diallyl terminated polyisobutylene having an average molecular weight of 5000 g/mole.

In yet another embodiment, component (B) is selected from a $R^2$—$Y^5$—$R^2$ compound, herein denoted as ($B^5$), where $R^2$ is as defined above and $Y^5$ is a hydrocarbon-silicone copolymer group. The hydrocarbon-silicone copolymer group may have the formula —$[R^1{}_u(R_2SiO)_v]_q$— where $R^1$ and R are as defined above;
u and v are independently $≧1$, alternatively u ranges from 1 to 20,
alternatively v ranges from 2 to 500, or from 2 to 200,
q is $>1$, alternatively q ranges from 2 to 500, alternatively q ranges from 2 to 100.

$R^2$—$Y^5$—$R^2$ compounds having a hydrocarbon-silicone copolymer group may be prepared via a hydrosilylation reaction between an α-ω unsaturated hydrocarbon, such as those described above as $B^1$, and an organohydrogensiloxane. A representative, non-limiting example of such a reaction is shown below.

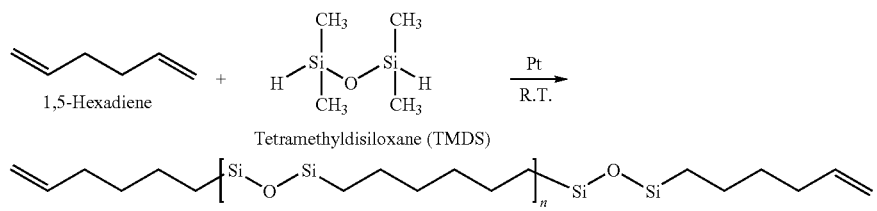

Component (B) may also be a mixture of any diene, diyne or ene-yne compound, such as any combinations of $B^1$, $B^2$, $B^3$, $B^4$, and $B^5$.

The amounts of component (A) and component (B) used to prepare the present composition will depend on the individual components and the desired SiH to aliphatic unsaturation ratio. The ratio of SiH in component (A) to aliphatic unsaturation from component (B) useful to prepare the compositions of the present invention can be from 10:1 to 1:10, alternatively 5:1 to 1:5, or alternatively 4:1 to 1:4.

If components (A) and (B) are not the only materials containing aliphatic unsaturated groups and SiH-containing groups in the present composition, then the above ratios relate to the total amount of such groups present in the composition rather than only those components.

(C) The Hydrosilylation Catalyst

Component (C) comprises any catalyst typically employed for hydrosilylation reactions. It is preferred to use platinum group metal-containing catalysts. By platinum group it is meant ruthenium, rhodium, palladium, osmium, iridium and platinum and complexes thereof. Platinum group metal-containing catalysts useful in preparing the compositions of the present invention are the platinum complexes prepared as described by Willing, U.S. Pat. No. 3,419,593, and Brown et al, U.S. Pat. No. 5,175,325, each of which is hereby incorporated by reference to show such complexes and their preparation. Other examples of useful platinum group metal-containing catalysts can be found in Lee et al., U.S. Pat. No. 3,989,668; Chang et al., U.S. Pat. No. 5,036,117; Ashby, U.S. Pat. No. 3,159,601; Lamoreaux, U.S. Pat. No. 3,220,972; Chalk et al., U.S. Pat. No. 3,296,291; Modic, U.S. Pat. No. 3,516,946; Karstedt, U.S. Pat. No. 3,814,730; and Chandra et al., U.S. Pat. No. 3,928,629 all of which are hereby incorporated by reference to show useful platinum group metal-containing catalysts and methods for their preparation. The platinum-containing catalyst can be platinum metal, platinum metal deposited on a carrier such as silica gel or powdered charcoal, or a compound or complex of a platinum group metal. Preferred platinum-containing catalysts include chloroplatinic acid, either in hexahydrate form or anhydrous form, and or a platinum-containing catalyst which is obtained by a method comprising reacting chloroplatinic acid with an aliphatically unsaturated organosilicon compound such as divinyltetramethyldisiloxane, or alkene-platinum-silyl complexes as described in U.S. patent application Ser. No. 10/017,229, filed Dec. 7, 2001, such as $(COD)Pt(SiMeCl_2)_2$, where COD is 1,5-cyclooctadiene and Me is methyl. These alkene-platinum-silyl complexes may be prepared, for example by mixing 0.015 mole $(COD)PtCl_2$ with 0.045 mole COD and 0.0612 moles $HMeSiCl_2$.

The appropriate amount of the catalyst will depend upon the particular catalyst used. The platinum catalyst should be present in an amount sufficient to provide at least 2 parts per million (ppm), preferably 4 to 200 ppm of platinum based on total weight percent solids (all non-solvent ingredients) in the composition. It is highly preferred that the platinum is present in an amount sufficient to provide 4 to 150 weight ppm of platinum on the same basis. The catalyst may be added as a single species or as a mixture of two or more different species.

(D) The Carrier Fluid

The silicone elastomers may be contained in an optional carrier fluid (D). Although it is not required, typically the carrier fluid may be the same as the solvent used for conducting the hydrosilylation reaction as described above. Suitable carrier fluids include silicones, both linear and cyclic, organic oils, organic solvents and mixtures of these. Specific examples of solvents may be found in U.S. Pat. No. 6,200,581, which is hereby incorporated by reference for this purpose.

Typically, the carrier fluid is a low viscosity silicone or a volatile methyl siloxane or a volatile ethyl siloxane or a volatile methyl ethyl siloxane having a viscosity at 25° C. in the range of 1 to 1,000 mm$^2$/sec such as hexamethylcyclotrisiloxane, octamethylcyclotetrasiloxane, decamethylcyclopentasiloxane, dodecamethylcyclohexasiloxane, octamethyltrisiloxane, decamethyltetrasiloxane, dodecamethylpentasiloxane, tetradecamethylhexasiloxane, hexadeamethylheptasiloxane, heptamethyl-3-{(trimethylsilyl)oxy)}trisiloxane, hexamethyl-3,3,bis{(trimethylsilyl)oxy}trisiloxane pentamethyl{(trimethylsilyl)oxy}cyclotrisiloxane as well as polydimethylsiloxanes, polyethylsiloxanes, polymethylethylsiloxanes, polymethylphenylsiloxanes, polydiphenylsiloxanes.

Organic solvents may be exemplified by, but not limited to, aromatic hydrocarbons, aliphatic hydrocarbons, alcohols, aldehydes, ketones, amines, esters, ethers, glycols, glycol ethers, alkyl halides and aromatic halides. Hydrocarbons including isododecane, isohexadecane, Isopar L (C11-C13), Isopar H(C11-C12), hydrogentated polydecen. Ethers and esters including isodecyl neopentanoate, neopentylglycol heptanoate, glycol distearate, dicaprylyl carbonate, diethylhexyl carbonate, propylene glycol n butyl ether, ethyl-3 ethoxypropionate, propylene glycol methyl ether acetate, tridecyl neopentanoate, propylene glycol methylether acetate (PGMEA), propylene glycol methylether (PGME). octyldodecyl neopentanoate, diisobutyl adipate, diisopropyl adipate, propylene glycol dicaprylate/dicaprate, and octyl palmitate. Additional organic carrier fluids suitable as a stand alone compound or as an ingredient to the carrier fluid include fats, oils, fatty acids, and fatty alcohols.

The amount of carrier fluid is such that there is 0 to 98 weight percent, alternatively 0.5 to 90 weight percent, alternatively 5 to 80 weight percent, of carrier fluid in composition containing (A) and (B) and (I)); where the sum of (A), (B), and (D) is 100 weight percent.

E) Personal or Healthcare Active

Component E) is active selected from any personal or health care active. As used herein, a "personal care active" means any compound or mixtures of compounds that are known in the art as additives in the personal care formulations that are typically added for the purpose of treating hair or skin to provide a cosmetic and/or aesthetic benefit. A "healthcare active" means any compound or mixtures of compounds that are known in the art to provide a pharmaceutical or medical benefit. Thus, "healthcare active" include materials consider as an active ingredient or active drug ingredient as generally used and defined by the United States Department of Health & Human Services Food and Drug Administration, contained in Title 21, Chapter I, of the Code of Federal Regulations, Parts 200-299 and Parts 300-499.

Thus, active ingredient can include any component that is intended to furnish pharmacological activity or other direct effect in the diagnosis, cure, mitigation, treatment, or prevention of disease, or to affect the structure or any function of the body of a human or other animals. The phrase can include those components that may undergo chemical change in the manufacture of drug products and be present in drug products in a modified form intended to furnish the specified activity or effect.

Some representative examples of active ingredients include; drugs, vitamins, minerals; hormones; topical antimicrobial agents such as antibiotic active ingredients, antifungal active ingredients for the treatment of athlete's foot, jock itch, or ringworm, and acne active ingredients; astringent active ingredients; deodorant active ingredients; wart remover active ingredients; corn and callus remover active ingredients; pediculicide active ingredients for the treatment of head, pubic (crab), and body lice; active ingredients for the control of dandruff, seborrheic dermatitis, or psoriasis; and sunburn prevention and treatment agents.

Useful active ingredients for use in processes according to the invention include vitamins and its derivatives, including "pro-vitamins". Vitamins useful herein include, but are not limited to, Vitamin $A_1$, retinol, $C_2$-$C_{18}$ esters of retinol, vitamin E, tocopherol, esters of vitamin E, and mixtures thereof. Retinol includes trans-retinol, 1,3-cis-retinol, 11-cis-retinol, 9-cis-retinol, and 3,4-didehydro-retinol, Vitamin C and its derivatives, Vitamin $B_1$, Vitamin $B_2$, Pro Vitamin B5, panthenol, Vitamin $B_6$, Vitamin $B_{12}$, niacin, folic acid, biotin, and pantothenic acid. Other suitable vitamins and the INCI names for the vitamins considered included herein are ascorbyl dipalmitate, ascorbyl methylsilanol pectinate, ascorbyl palmitate, ascorbyl stearate, ascorbyl glucocide, sodium ascorbyl phosphate, sodium ascorbate, disodium ascorbyl sulfate, potassium (ascorbyl/tocopheryl)phosphate.

RETINOL, it should be noted, is an International Nomenclature Cosmetic Ingredient Name (INCI) designated by The Cosmetic, Toiletry, and Fragrance Association (CTFA), Washington D.C., for vitamin A. Other suitable vitamins and the INCI names for the vitamins considered included herein are RETINYL ACETATE, RETINYL PALMITATE, RETINYL PROPIONATE, α-TOCOPHEROL, TOCOPHERSOLAN, TOCOPHERYL ACETATE, TOCOPHERYL LINOLEATE, TOCOPHERYL NICOTINATE, and TOCOPHERYL SUCCINATE.

Some examples of commercially available products suitable for use herein are Vitamin A Acetate and Vitamin C, both products of Fluka Chemie AG, Buchs, Switzerland; COVI-OX T-50, a vitamin E product of Henkel Corporation, La Grange, Ill.; COVI-OX T-70, another vitamin E product of Henkel Corporation, La Grange, Ill.; and vitamin E Acetate, a product of Roche Vitamins & Fine Chemicals, Nutley, N.J.

The active ingredient used in processes according to the invention can be an active drug ingredient. Representative examples of some suitable active drug ingredients which can be used are hydrocortisone, ketoprofen, timolol, pilocarpine, adriamycin, mitomycin C, morphine, hydromorphone, diltiazem, theophylline, doxorubicin, daunorubicin, heparin, penicillin G, carbenicillin, cephalothin, cefoxitin, cefotaxime, 5-fluorouracil, cytarabine, 6-azauridine, 6-thioguanine, vinblastine, vincristine, bleomycin sulfate, aurothioglucose, suramin, mebendazole; clonidine, scopolamine, propranolol, phenylpropanolamine hydrochloride, ouabain, atropine, haloperidol, isosorbide, nitroglycerin, ibuprofen, ubiquinones, indomethacin, prostaglandins, naproxen, salbutamol, guanabenz, labetalol, pheniramine, metrifonate, and steroids.

Considered to be included herein as active drug ingredients for purposes of the present invention are antiacne agents such as benzoyl peroxide and tretinoin; antibacterial agents such as chlorohexadiene gluconate; antifungal agents such as miconazole nitrate; anti-inflammatory agents; corticosteroidal drugs; non-steroidal anti-inflammatory agents such as diclofenac; antipsoriasis agents such as clobetasol propionate; anesthetic agents such as lidocaine; antipruritic agents; antidermatitis agents; and agents generally considered barrier films.

The active component E) of the present invention can be a protein, such as an enzyme. The internal inclusion of enzymes in the silicone elastomer gel have advantages to prevent enzymes from deactivating and maintain bioactive effects of enzymes for longer time. Enzymes include, but are not limited to, commercially available types, improved types, recombinant types, wild types, variants not found in nature, and mixtures thereof. For example, suitable enzymes include hydrolases, cutinases, oxidases, transferases, reductases, hemicellulases, esterases, isomerases, pectinases, lactases, peroxidases, laccases, catalases, and mixtures thereof. Hydrolases include, but are not limited to, proteases (bacterial, fungal, acid, neutral or alkaline), amylases (alpha or beta), lipases, mannanases, cellulases, collagenases, lisozymes, superoxide dismutase, catalase, and mixtures thereof. Said protease include, but are not limited to, trypsin, chymotrypsin, pepsin, pancreatin and other mammalian enzymes; papain, bromelain and other botanical enzymes; subtilisin, epidermin, nisin, naringinase(L-rhammnosidase) urokinase and other bacterial enzymes. Said lipase include, but are not limited to, triacyl-glycerol lipases, monoacylglycerol lipases, lipoprotein lipases, e.g. steapsin, erepsin, pepsin, other mammalian, botanical, bacterial lipases and purified ones. Natural papain is preferred as said enzyme. Further, stimulating hormones, e.g. insulin, can be used together with these enzymes to boost the effectiveness of them.

Component E) may also be a sunscreen agent. The sunscreen agent can be selected from any sunscreen agent known in the art to protect skin from the harmful effects of exposure to sunlight. The sunscreen compound is typically chosen from an organic compound, an inorganic compound, or mixtures thereof that absorbs ultraviolet (UV) light. Thus, representative non limiting examples that can be used as the sunscreen agent include; Aminobenzoic Acid, Cinoxate, Diethanolamine Methoxycinnamate, Digalloyl Trioleate, Dioxybenzone, Ethyl 4-[bis(Hydroxypropyl)] Aminobenzoate, Glyceryl Aminobenzoate, Homosalate, Lawsone with Dihydroxyacetone, Menthyl Anthranilate, Octocrylene, Octyl Methoxycinnamate, Octyl Salicylate, Oxybenzone, Padimate O, Phenylbenzimidazole Sulfonic Acid, Red Petrolatum, Sulisobenzone, Titanium Dioxide, and Trolamine Salicylate, cetarninosalol, Allatoin PABA, Benzalphthalide, Benzophenone, Benzophenone 1-12, 3-Benzylidene Camphor, Benzylidenecamphor Hydrolyzed Collagen Sulfonamide, Benzylidene Camphor Sulfonic Acid, Benzyl Salicylate, Bomelone, Bumetriozole, Butyl Methoxydibenzoylmethane, Butyl PABA, Ceria/Silica, Ceria/Silica Talc, Cinoxate, DEA-Methoxycinnamate, Dibenzoxazol Naphthalene, Di-t-Butyl Hydroxybenzylidene Camphor, Digalloyl Trioleate, Diisopropyl Methyl Cinnamate, Dimethyl PABA Ethyl Cetearyldimonium Tosylate, Dioctyl Butamido Triazone, Diphenyl Carbomethoxy Acetoxy Naphthopyran, Disodium Bisethylphenyl Tiamminotriazine Stilbenedisulfonate, Disodium Distyrylbiphenyl Triaminotriazine Stilbenedisulfonate, Disodium Distyrylbiphenyl Disulfonate, Drometrizole, Drometrizole Trisiloxane, Ethyl Dihydroxypropyl PABA, Ethyl Diisopropylcinnamate, Ethyl Methoxycinnamate, Ethyl PABA, Ethyl Urocanate, Etrocrylene Ferulic Acid, Glyceryl Octanoate Dimethoxycinnamate, Glyceryl PABA, Glycol Salicylate, Homosalate, Isoamyl p-Methoxycinnamate, Isopropylbenzyl Salicylate, Isopropyl Dibenzolylmethane, Isopropyl Methoxycinnamate, Menthyl Anthranilate, Menthyl Salicylate, 4-Methylbenzylidene, Camphor, Octocrylene, Octrizole, Octyl Dimethyl PABA, Octyl Methoxycinnamate, Octyl Salicylate, Octyl Triazone, PABA, PEG-25 PABA, Pentyl Dimethyl PABA, Phenylbenzimidazole Sulfonic Acid, Polyacrylamidomethyl Benzylidene Camphor, Potassium Methoxycinnamate, Potassium Phenylbenzimidazole Sulfonate, Red Petrolatum, Sodium Phenylbenzimidazole Sulfonate, Sodium Urocanate, TEA-Phenylbenzimidazole Sulfonate, TEA-Salicylate, Terephthalylidene Dicamphor Sulfonic Acid, Titanium Dioxide, Zinc Dioxide, Serium Dioxide, TriPABA Panthenol, Urocanic Acid, and VA/Crotonates/Methacryloxybenzophenone-1 Copolymer.

The sunscreen agent can be a single one or combination of more than one. Alternatively, the sunscreen agent is a cinnamate based organic compound, or alternatively, the sunscreen agent is octyl methoxycinnamate, such as Uvinul® MC 80 an ester of para-methoxycinnamic acid and 2-ethylhexanol.

Component E) may also be a fragrance or perfume. The perfume can be any perfume or fragrance active ingredient commonly used in the perfume industry. These compositions typically belong to a variety of chemical classes, as varied as alcohols, aldehydes, ketones, esters, ethers, acetates, nitrites, terpenic hydrocarbons, heterocyclic nitrogen or sulfur containing compounds, as well as essential oils of natural or synthetic origin. Many of these perfume ingredients are described in detail in standard textbook references such as Perfume and Flavour Chemicals, 1969, S. Arctander, Montclair, N.J.

Fragrances may be exemplified by, but not limited to, perfume ketones and perfume aldehydes. Illustrative of the perfume ketones are buccoxime; iso jasmone; methyl beta naphthyl ketone; musk indanone; tonalid/musk plus; Alpha-Damascone, Beta-Damascone, Delta-Damascone, Iso-Damascone, Damascenone, Damarose, Methyl-Dihydrojasmonate, Menthone, Carvone, Camphor, Fenchone, Alpha-lonone, Beta-lonone, Gamma-Methyl so-called lonone, Fleuramone, Dihydrojasmone, Cis-Jasmone, Iso-E-Super, Methyl-Cedrenyl-ketone or Methyl-Cedrylone, Acetophenone, Methyl-Acetophenone, Para-Methoxy-Acetophenone, Methyl-Beta-Naphtyl-Ketone, Benzyl-Acetone, Benzophenone, Para-Hydroxy-Phenyl-Butanone, Celery Ketone or Livescone, 6-Isopropyldecahydro-2-naphtone, Dimethyl-Octenone, Freskomenthe, 4-(1-Ethoxyvinyl)-3,3,5,5,-tetramethyl-Cyclohexanone, Methyl-Heptenone, 2-(2-(4-Methyl-3-cyclohexen-1-yl)propyl)-cyclopentanone, 1-(p-Menthen-6(2)-yl)-1-propanone, 4-(4-Hydroxy-3-methoxyphenyl)-2-butanone, 2-Acetyl-3,3-Dimethyl-Norbornane, 6,7-Dihydro-1,1,2,3,3-Pentamethyl-4(5H)-Indanone, 4-Damascol, Dulcinyl or Cassione, Gelsone, Hexylon, Isocyclemone E, Methyl Cyclocitrone, Methyl-Lavender-Ketone, Orivon, Para-tertiary-Butyl-Cyclohexanone, Verdone, Delphone, Muscone, Neobutenone, Plicatone, Veloutone, 2,4,4,7-Tetramethyl-oct-6-en-3-one, and Tetrameran.

More preferably, the perfume ketones are selected for its odor character from Alpha Damascone, Delta Damascone, Iso Damascone, Carvone, Gamma-Methyl-lonone, Iso-E-Super, 2,4,4,7-Tetramethyl-oct-6-en-3-one, Benzyl Acetone, Beta Damascone, Damascenone, methyl dihydrojasmonate, methyl cedrylone, and mixtures thereof.

Preferably, the perfume aldehyde is selected for its odor character from adoxal; anisic aldehyde; cymal; ethyl vanillin; florhydral; helional; heliotropin; hydroxycitronellal; koavone; lauric aldehyde; lyral; methyl nonyl acetaldehyde; P. T. bucinal; phenyl acetaldehyde; undecylenic aldehyde; vanillin; 2,6,10-trimethyl-9-undecenal, 3-dodecen-1-al, alpha-n-amyl cinnamic aldehyde, 4-methoxybenzaldehyde, benzaldehyde, 3-(4-tert butylphenyl)-propanal, 2-methyl-3-(para-methoxyphenyl propanal, 2-methyl-4-(2,6,6-trimethyl-2(1)-cyclohexen-1-yl) butanal, 3-phenyl-2-propenal, cis-/trans-3,7-dimethyl-2,6-octadien-1-al, 3,7-dimethyl-6-octen-1-al, [(3,7-dimethyl-6-octenyl)oxy]acetaldehyde, 4-isopropylbenzyaldehyde, 1,2,3,4,5,6,7,8-octahydro-8,8-dimethyl-2-naphthaldehyde, 2,4-dimethyl-3-cyclohexen-1-carboxaldehyde, 2-methyl-3-(isopropylphenyl)propanal, 1-decanal; decyl aldehyde, 2,6-dimethyl-5-heptenal, 4-(tricyclo[5.2.1.0(2,6)]-decylidene-8)-butanal, octahydro-4,7-methano-1H-indenecarboxaldehyde, 3-ethoxy-4-hydroxy benzaldehyde, para-ethyl-alpha,alpha-dimethyl hydrocinnamaldehyde, alpha-methyl-3,4-(methylenedioxy)-hydrocinnamaldehyde, 3,4-methylenedioxybenzaldehyde, alpha-n-hexyl cinnamic aldehyde, m-cymene-7-carboxaldehyde, alpha-methyl phenyl acetaldehyde, 7-hydroxy-3,7-dimethyl octanal, Undecenal, 2,4,6-trimethyl-3-cyclohexene-1-carboxaldehyde, 4-(3)(4-methyl-3-pentenyl)-3-cyclohexen-carboxaldehyde, 1-dodecanal, 2,4-dimethyl cyclohexene-3-carboxaldehyde, 4-(4-hydroxy-4-methyl pentyl)-3-cylohexene-1-carboxaldehyde, 7-methoxy-3,7-dimethyloctan-1-al, 2-methyl undecanal, 2-methyl decanal, 1-nonanal, 1-octanal, 2,6,10-trimethyl-5,9-undecadienal, 2-methyl-3-(4-tertbutyl) propanal, dihydrocinnamic aldehyde, 1-methyl-4-(4-methyl-3-pentenyl)-3-cyclohexene-1-carbox aldehyde, 5 or 6 methoxyl 0 hexahydro-4,7-methanoindan-1 or 2-carboxaldehyde, 3,7-dimethyloctan-1-al, 1-undecanal, 10-undecen-1-al, 4-hydroxy-3-methoxy benzaldehyde, 1-methyl-3-(4-methylpentyl)-3-cyclhexenecarboxaldehyde, 7-hydroxy-3,7-dimethyl octanal, trans-4-decenal, 2,6-nonadienal, paratolylacetaldehyde; 4-methylphenylacetaldehyde, 2-methyl-4-(2,6,6-trimethyl-1-cyclohexen-1-yl)-2-butena 1, ortho-methoxycinnamic aldehyde, 3,5,6-trimethyl-3-cyclohexene carboxaldehyde, 3,7-dimethyl-2-methylene-6-octenal, phenoxyacetaldehyde, 5,9-dimethyl-4,8-decadienal, peony aldehyde (6,10-dimethyl-3-oxa-5,9-undecadien-1-al), hexahydro-4,7-methanoindan-1-carboxaldehyde, 2-methyl octanal, alpha-methyl-4-(1-methyl ethyl)benzene acetaldehyde, 6,6-dimethyl-2-norpinene-2-propionaldehyde, para methyl phenoxy acetaldehyde, 2-methyl-3-phenyl-2-propen-1-al, 3,5,5-trimethylhexanal, Hexahydro-8,8-dimethyl-2-naphthaldehyde, 3-propyl-bicyclo[2.2.1]-hept-5-ene-2-carbaldehyde, 9-decenal, 3-methyl-5-phenyl-1-pentanal, methylnonyl acetaldehyde, hexanal, trans-2-hexenal, 1-p-menthene-q-carboxaldehyde and mixtures thereof.

More preferred aldehydes are selected for their odor character from 1-decanal, benzaldehyde, florhydral, 2,4-dimethyl-3-cyclohexen-1-carboxaldehyde; cis/trans-3,7-dimethyl-2,6-octadien-1-al; heliotropin; 2,4,6-trimethyl-3-cyclohexene-1-carboxaldehyde; 2,6-nonadienal; alpha-n-amyl cinnamic aldehyde, alpha-n-hexyl cinnamic aldehyde, P.T. Bucinal, lyral, cymal, methyl nonyl acetaldehyde, hexanal, trans-2-hexenal, and mixture thereof.

In the above list of perfume ingredients, some are commercial names conventionally known to one skilled in the art, and also includes isomers. Such isomers are also suitable for use in the present invention.

Component E) may also be one or more plant extract. Examples of these components are as follows: Ashitaba extract, avocado extract, hydrangea extract, Althea extract, Arnica extract, aloe extract, apricot extract, apricot kernel extract, *Ginkgo Biloba* extract, fennel extract, turmeric[*Curcuma*] extract, oolong tea extract, rose fruit extract, Echinacea extract, Scutellaria root extract, Phellodendro bark extract, Japanese Coptis extract, Barley extract, Hyperium extract, White Nettle extract, Watercress extract, Orange extract, Dehydrated saltwater, seaweed extract, hydrolyzed elastin, hydrolyzed wheat powder, hydrolyzed silk, Chamomile extract, Carrot extract, Artemisia extract, Glycyrrhiza extract, hibiscustea extract, Pyracantha Fortuneana Fruit extract, Kiwi extract, Cinchona extract, cucumber extract, guanocine, Gardenia extract, Sasa Albo-marginata extract, Sophora root extract, Walnut extract, Grapefruit extract, Clematis extract, Chlorella extract, mulberry extract, Gentiana extract, black tea extract, yeast extract, burdock extract, rice bran ferment extract, rice germ oil, comfrey extract, collagen, cowberry extract, Gardenia extract, Asiasarum Root extract, Family of Bupleurum extract, umbilical cord extract, Salvia extract, Saponaria extract, Bamboo extract, Crataegus fruit extract, Zanthoxylum fruit extract, shiitake extract, Rehmannia root extract, gromwell extract, *Perilla* extract, linden extract, Filipendula extract, peony extract, Calamus Root extract, white birch extract, Horsetail extract, Hedera Helix(Ivy) extract, hawthorn extract, *Sambucus nigra* extract, Achillea millefolium extract, *Mentha piperita* extract, sage extract, mallow extract, Cnidium officinale Root extract, Japanese green gentian extract, soybean extract, jujube extract, thyme extract, tea extract, clove extract, Gramineae *imperata* cyrillo extract, *Citrus unshiu* peel extract Japanese Angellica Root extract, Calendula extract, Peach Kernel extract, Bitter orange peel extract, Houttuyna cordata extract, tomato extract, natto extract, Ginseng extract, Green tea extract (camelliea sinesis), garlic extract, wild rose extract, hibiscus extract, Ophiopogon tuber extarct, Nelumbo nucifera extract, parsley extract, honey, hamamelis extract, *Parietaria* extract, Isodonis herba extract, bisabolol extract, Loquat extract, coltsfoot extract, butterbur extract, Porid cocos wolf extract, extract of butcher's broom, grape extract, propolis extract, *luffa* extract, safflower extract, peppermintextract, linden tree extract, Paeonia extract, hop extract, pine tree extract, horse chestnut extract, Mizu-bashou [Lysichiton camtschatcese] extract, Mukurossi peel extract, Melissa extract, peach extract, cornflower extract, eucalyptus extract, saxifrage extract, citron extract, *coix* extract, mugwort extract, lavender extract, apple extract, lettuce extract, lemon extract, Chinese milk vetch extract, rose extract, rosemary extract, Roman Chamomile extract, and royal jelly extract.

The amount of component E) present in the silicone gel composition may vary, but typically range as follows;

0.05 to 50 wt %, alternatively 1 to 25 wt %, or alternatively 1 to 10 wt %, based on the amount by weight of silicone elastomer gel present in the composition, that is total weight of components A), B), C) and D) in the silicone gel composition.

The active, component E), may be added to the silicone gel composition either during the making of the silicone elastomer (pre-load method), or added after the formation of the silicone elastomer gel (post load method).

The pre-load method involves;

I) reacting;
 a) an organohydrogencyclosiloxane having at least two SiH units on a siloxane ring,
 B) a compound or mixture of compounds having at least two aliphatic unsaturated hydrocarbon groups in its molecules,
 C) a hydrosilylation catalyst, to form
 A) an organohydrogensiloxane having at least two SiH containing cyclosiloxane rings in its molecule,
wherein the molar ratio of the SiH units of component a) to the aliphatic unsaturated hydrocarbon groups of component B) ranges from 2/1 to 8/1, II) reacting;
 A) the organohydrogensiloxane having at least two SiH containing cyclosiloxane rings in its molecule, with additional quantities of
 B) the compound containing at least two aliphatic unsaturated hydrocarbon groups in its molecules,
 C) the hydrosilylation catalyst, in the presence of
 D) an optional carrier fluid, and
 E) a personal care or healthcare active, to form the silicone elastomer gel.

The post-load method involves;

I) reacting;
 a) an organohydrogencyclosiloxane having at least two SiH units on a siloxane ring,
 B) a compound or mixture of compounds having at least two aliphatic unsaturated groups in its molecules,
 C) a hydrosilylation catalyst to form
 A) an organohydrogensiloxane having at least two SiH containing cyclosiloxane rings in its molecule,
wherein the molar ratio of the SiH units of component a) to the aliphatic unsaturated groups of component B) ranges from 2/1 to 8/1, II) further reacting;
 A) the organohydrogensiloxane having at least two SiH containing cyclosiloxane rings in its molecule, with additional quantities of
 B) the compound containing at least two aliphatic unsaturated groups in its molecules,
 C) the hydrosilylation catalyst, in the presence of
 D) an optional carrier fluid to form a silicone elastomer gel, III) admixing
 E) a personal care or healthcare active with the silicone elastomer gel to form the silicone elastomer gel containing active.

The Silicone Elastomer

The silicone elastomers of the present invention are obtainable as hydrosilylation reaction products of components A), B), and C). The term "hydrosilylation" means the addition of an organosilicon compound containing silicon-bonded hydrogen, (such as component A) to a compound containing aliphatic unsaturation (such as component B), in the presence of a catalyst (such as component C). Hydrosilylation reactions are known in the art, and any such known methods or techniques may be used to effect the hydrosilylation reaction of components A), B), and C) to prepare the silicone elastomers of the present invention.

The hydrosilylation reaction may be conducted in the presence of a solvent, and the solvent subsequently removed by known techniques. Alternatively, the hydrosilylation may be conducted in a solvent, where the solvent is the same as the carrier fluid described as optional component D).

Alternatively, the silicone elastomers may be prepared by a process comprising:
I) reacting;
a) an organohydrogencyclosiloxane having at least two SiH units on a siloxane ring,
B) a compound or mixture of compounds having at least two aliphatic unsaturated hydrocarbon groups in its molecules,
C) a hydrosilylation catalyst to form
A) an organohydrogensiloxane having at least two SiH containing cyclosiloxane rings in its molecule,
wherein the molar ratio of the SiH units of component a) to the aliphatic unsaturated groups of component B) ranges from 2/1 to 8/1,
alternatively from 2/1 to 6/1,
or alternatively from 3/1 to 4/1,
II) further reacting;
A) the organohydrogensiloxane having at least two SiH containing cyclosiloxane rings in its molecule, with additional quantities of
B) the compound containing at least two aliphatic unsaturated groups in its molecules,
C) the hydrosilylation catalyst. to form a silicone elastomer.

Components a, A), B), C) are the same as those described above. Also, the reaction may be conducted under similar conditions as described above.
In aforementioned step II) the molar ratio of the SiH units of component A) to the aliphatic unsaturated groups of component B) ranges from 10/1 to 1/10,
alternatively from 5/1 to 1/5,
or alternatively from 4/1 to 1/4.

Gelled Compositions Containing the Silicone Elastomer

The silicone elastomers can be added to a carrier fluid (as described above as component D) to form gelled compositions, or alternatively be prepared first in a separate reaction and then added to the carrier fluid to obtain a gel. The gelled compositions of the present invention may be characterized by their hardness or firmness. Useful tests to characterize the gels are those recommended by the Gelatin Manufacturers Institute of America such as the use of a "Texture Analyzer" (model TA.XT2, Stable Micro Systems, Inc., Godalming, England). The gel sample is subject to a compression test with the Texture Analyzer having a probe with a 5.0 kg load cell. The probe approaches the surface of the gel at a speed of 0.5 mm/sec and continues compression into the gel to a distance of 5.0 mm, then holds for 1 second before retreating. The Texture Analyzer detects the resistance force the probe experiences during the compression test. The force exhibited by the load cell is plotted as a function of time.

The hardness of the silicone elastomers, gels and elastomer blends (SEBs) for purposes of this invention is defined as the resistance force detected by the probe of the "Texture Analyzer" during the compression test. Two data may used to characterize hardness: Force 1, the force at the maximum compression point (i.e. the 5.0 mm compression point into the gel surface), and Area F-T: the area-force integration during the 1 second hold at the maximum compression point. The average of a total of 5 tests are typically performed for each gel The value obtained for Force 1 is converted into Newton (N), by dividing the gram force value by 101.97. (i.e. 1 Newton equals 101.97 g force based on the size of the probe used in this instrument). The second property reported by Texture Analyzer measurement is Area F-T 1:2, in g force-sec. This is the area integration of the force vs. test time cure. This property is indicative of a gel network since it indicates ability to sustain resistance to the compression force, which is relevant to elastomers and gels. The value is reported in g force-sec, and is converted to Newton·sec in SI unit by dividing the value in g force·sec by 101.97.

The silicone gels of the present invention has a compression hardness of at least 200 Newton/$m^2$, alternatively 400 Newton/$m^2$_, or alternatively 600 Newton/$m^2$.

Gel Paste Compositions Containing the Silicone Elastomer

The gelled compositions of the present invention can be used to prepare gel paste or gel blend compositions containing actives by;
I) shearing the silicone elastomer gel, as described above,
II) combining the sheared silicone elastomer gel with additional quantities of
D) the carrier fluid, as described above, and optionally
E) a personal or health care active
to form a gel paste or blend composition.

The silicone elastomer gel compositions of the present invention blends may be considered as discrete crosslinked silicone elastomer gel particles dispersed in carrier fluids. Thus, the silicone elastomer compositions are effective rheological thickeners for lower molecular weight silicone fluids. As such they can be used to prepare useful gel blend compositions, such as "paste" compositions.

To make such silicone elastomer blends, the aforementioned silicone elastomer gels of known initial elastomer content (IEC) are sheared to obtain small particle size and further diluted to a final elastomer content (FEC). "Shearing", as used herein refers to any shear mixing process, such as obtained from homogenizing, sonalating, or any other mixing processes known in the art as shear mixing. The shear mixing of the silicone elastomer gel composition results in a composition having reduced particle size. The subsequent composition having reduced particle size is then further combined with D) the carrier fluid. The carrier fluid may be any carrier fluid as described above, but typically is a volatile methyl siloxane, such as D5. The technique for combining the D) the carrier fluid with the silicone elastomer composition having reduced particle size is not critical, and typically involves simple stirring or mixing. The resulting compositions may be considered as a paste, having a viscosity greater than 100,000 cP (mPa·s).

EXAMPLES

These examples are intended to illustrate the invention to one of ordinary skill in the art and are should not be interpreted as limiting the scope of the invention set forth in the claims.

Materials Description

The following materials were used in these examples.

Organohydrogensiloxanes

MeH CYCLICS=methylhydrogen cyclosiloxanes (MeH cyclics) having the formula $[(CH_3)HSiO]_x$ where the average value of x is 4.4.

MeH LINEAR=an organohydrogenpolysiloxane have the average formula $MD_{94}D'_6M$ Siloxane Polymers Containing Unsaturated Groups VINYL SILOXANE #1=a dimethylvinylsiloxy-terminated dimethylpolysiloxane of the general formula $(CH_2\!\!=\!\!CH)(CH_3)_2SiO[(CH_3)_2SiO]_{dp}Si(CH_3)_2(CH\!\!=\!\!CH_2)$, where the average degree of polymerization (dp) was 8 and having a viscosity of 4 $mm^2$/s at 25° C.

VINYL SILOXANE #2=a dimethylvinylsiloxy-terminated dimethylpolysiloxane of the general formula $(CH_2\!\!=\!\!CH)(CH_3)_2SiO[(CH_3)_2SiO]_{dp}Si(CH_3)_2(CH\!\!=\!\!CH_2)$, where the average degree of polymerization (dp) was 130 and having a viscosity of 325 mm²/s at 25° C.

VINYL SILOXANE #3=[(CH$_2$H)(CH$_3$)$_2$SiO[(CH$_3$)$_2$SiO]$_4$]Si

VINYL SILOXANE #4=tetramethyltetravinylcyclotetrasiloxane [(CH$_2$=CH)(CH$_3$)SiO]$_4$ VINYL SILOXANE #5=a dimethylvinylsiloxy-terminated dimethylpolysiloxane of the general formula (CH$_2$=CH)(CH$_3$)$_2$SiO[(CH$_3$)$_2$SiO]$_{dp}$Si(CH$_3$)$_2$(CH=CH$_2$), where the average degree of polymerization (dp) was 27 and having a viscosity of 25 mm²/s at 25° C.

VINYL SILOXANE #6=a dimethylhexenylsiloxy-terminated dimethylpolysiloxane of the general formula (CH$_2$=CH(CH$_2$)$_4$)(CH$_3$)$_2$SiO[(CH$_3$)$_2$SiO]$_{dp}$Si(CH$_3$)$_2$((CH$_2$)$_4$(CH$_2$=CH)), where the average degree of polymerization (dp) was 37 and a viscosity of 40 mm²/s at 25° C.

VINYL SILOXANE #7=a dimethylhexenylsiloxy-terminated dimethylpolysiloxane of the general formula (CH$_2$=CH(CH$_2$)$_4$)(CH$_3$)$_2$SiO[(CH$_3$)$_2$SiO]$_{dp}$Si(CH$_3$)$_2$((CH$_2$)$_4$(CH$_2$=CH), where the average degree of polymerization (dp) was 100 and a viscosity of 170 mm²/s at 25° C.

VINYL SILOXANE #8=a dimethylhexenylsiloxy-terminated dimethylpolysiloxane of the general formula (CH$_2$=CH(CH$_2$)$_4$)(CH$_3$)$_2$SiO[(CH$_3$)$_2$SiO]$_{dp}$Si(CH$_3$)$_2$((CH$_2$)$_4$(CH$_2$=CH)), where the average degree of polymerization (dp) was 200 and a viscosity of 730 min²/s at 25° C.

VINYL SILOXANE #9=a dimethylvinylsiloxy-terminated dimethylpolysiloxane of the general formula (CH$_2$=CH)(CH$_3$)$_2$SiO[(CH$_3$)$_2$SiO]$_{dp}$Si(CH$_3$)$_2$(CH=CH$_2$), where the average degree of polymerization (dp) was 27.

VINYL SILOXANE #10=a dimethylvinylsiloxy-terminated dimethylpolysiloxane of the general formula (CH$_2$=CH)(CH$_3$)$_2$SiO[(CH$_3$)$_2$SiO]$_{dp}$Si(CH$_3$)$_2$(CH=CH$_2$), where the average degree of polymerization (dp) was 430.

Hydrosilylation Catalyst

PT CATALYST=SLY-OFF 4000 (Dow Corning Corporation, Midland Mich.) Pt catalyst used as provided containing 0.52 weight % Pt.

Carrier Fluids

D5=decamethylcyclopentasiloxane or D5 cyclics, DC245 (Dow Corning Corporation, Midland Mich.) used as provided.

IDNP=isodecyl neopentanoate obtained from ISP (International Specialty Products Co) under the trade name of CERAPHYL SLK.

IDD=isododecane

Stabilizer=Vitamin A palmitate (VAP) and butylated hydroxytoluene (BHT)

Methods of Measuring Viscosity of Silicone Elastomer Blends (SEBs)

The Brookfield Helipath™ Stand, when used with a suitable Brookfield Viscometer fitted with a special T-bar type spindle, will permit viscosity/consistency measurements in centipoise values for materials having characteristics similar to paste, putty, cream, gelatin, or wax.

The viscosity of silicone elastomer blends was determined using a Brookfield Model RVD-II+Viscometer with Helipath stand (Brookfield Model D) and T-Bar spindles (Brookfield Helipath Spindle Set). All were purchased from Brookfield Engineering Laboratories, Inc. (11 Commerce Boulevard Middleboro, Mass., USA).

A sample size of 100 g in a 4 oz. round jar was required. The following preparation procedure was used before measurement: the sample was de-aired first via centrifuge, then vacuum de-aired for two hours. After de-airing, the sample was conditioned for a minimum of 4 hours @ 25° C. The sample was positioned with T-bar spindle at center. The reading was taken according to the typical procedure for Helipath spindle.

In general, spindle 93 (T-bar spindle C) is used for the less viscous sample, spindle 95 (T-bar spindle E) for the more viscous samples. The standard setting for rpm was 2.5. The spindle speed is maintained at constant 2.5 rpm and spindle was varied to handle samples with significant viscosities.

Measurement of Silicone Elastomer Gel Hardness

The hardness (or firmness) of silicone elastomer gels was characterized using a Texture analyzer (model TA.XT2, Stable Micro Systems, Inc., Godalming, England). The Gelatin Manufacturers Institute of America recommends such test methods as a standard procedure.

For silicone gels and elastomer blends, a ½ inch (1.27 cm) diameter cylindrical probe made of DELRIN acetal resin (Dupont) was used for the measurement. The gel sample is subject to the compression test using the probe with the following test cycle: the probe approaches the surface of the gel at a speed of 0.5 mm/sec and continues compression into the gel to a distance of 5.0 mm, then holds for 1 second before retreating. The Texture Analyzer has a 5.0 Kg load cell to detect the resistance force the probe experiences during the compression test. The force exhibited by the load cell is plotted as a function of time.

The hardness of the silicone elastomers, gels and elastomer blends (SEBs) is defined as the resistance force detected by the probe during the compression test. Two data are used for the hardness value: Force 1: the force at the maximum compression point (i.e. the 5.0 mm compression point into the gel surface), and Area F-T: the area-force integration during the 1 second hold at the maximum compression point. A total of 5 tests were performed for each gel and the average of the five tests is reported.

Texture Analyzer used for gel hardness measurement is force in gram, as detected by the transducer. Two values are reported for gel hardness: Force 1, the force in gram registered when the probe reached its pre-programmed full indentation (or compression) in gel sample. The unit for Force 1 reading is gram force.

The value obtained for Force 1 is converted into Newton (N), by dividing the gram force value by 101.97. (i.e. 1 Newton equals 101.97 g force based on the size of the probe used in this instrument). For instance, a value of 6327 g force converts to 62.0 N.

The second property reported by Texture Analyzer measurement is Area F-T 1:2, in g force·sec. This is the area integration of the force vs. test time cure. This is an indicative property of a gel network as it indicates it ability to sustain resistance to the compression force, which is relevant to elastomers and gels.

The value is reported in g force·sec, and is converted to Newton·sec in SI unit by dividing the value in g force·sec by 101.97. For instance, a value of 33,947 g force·sec is 332.9 N·s in SI units.

Example 1

Reference

Preparation Clan Organohydrogensiloxane Having at Least Two SiH Containing Cyclosiloxane Rings with a Short Spacer Between the Rings Cyclic SiH-containing siloxanes, that is a representative Component A)'s, were made by reacting MeH cyclics with VINYL SILOXANE #1, a dimethylinyl-ended silicone having on average 8 dimethylsiloxane units (DP=8), in the presence of Pt catalyst The specific [SiH]/[Vi] ratio was kept at 3.0, 3.42, and 4.0 for the three examples and the reaction was conducted at 40° C. The finished polymers were clear liquids having the general structures shown in

TABLE 1

The SiH contents of these siloxanes were found to be 0.374%, 0.432%, and 0.505% respectively.

| Example # | 1A |
|---|---|
| [SiH]/[Vi] ratio | 3.00 |
| Component B | VINYL SILOXANE #1 |

Target structure

| % SiH in mixture | 100.0 |
|---|---|
| Wt. % H, theoretical | 0.374 |
| Cure temp/condition | 40° C. |

| Actual amount | Actual amount |
|---|---|
| MeH-cyclics | 67.730 |
| Component B, g | 132.2 |
| Pt Catalyst g | 0.19 |
| Total Batch, g | 200.12 |
| Mixture appearance | Clear, very viscous |

| Example # | 1B |
|---|---|
| [SiH]/[Vi] ratio | 3.42 |
| Component B | VINYL SILOXANE #1 |

Target structure

| % SiH in mixture | 100.0 |
|---|---|
| Wt. % H, theoretical | 0.432 |
| Cure temp/condition | 40° C. |

| Actual amount | Actual amount |
|---|---|
| MeH-cyclics | 73.720 |
| Component B, g | 126.32 |
| Pt Catalyst g | 0.19 |
| Total Batch, g | 200.23 |
| Mixture appearance | Clear, viscous |

| Example # | 1C |
|---|---|
| [SiH]/[Vi] ratio | 4.00 |
| Component B | VINYL SILOXANE #1 |

Target structure

| % SiH in mixture | 100.0 |
|---|---|
| Wt. % H, theoretical | 0.505 |
| Cure temp/condition | 40° C. |

| Actual amount | Actual amount |
|---|---|
| MeH-cyclics | 81.130 |
| Component B, g | 118.83 |

TABLE 1-continued

| | |
|---|---|
| Pt Catalyst g | 0.2 |
| Total Batch, g | 200.16 |
| Mixture appearance | Clear, viscous |

Example 2

Reference

Preparation of an Organohydrogensiloxane Having at Least Two SiH Containing Cyclosiloxane Rings with a Long Spacer Cyclic SiH-containing siloxanes (representative component A)) having a linear structure with longer spacer were made by reacting MeH-cyclics with VINYL SILOXANE #2 (DP*=130) in the presence of a Pt catalyst. The [SiH]/[Vi] ratios were 3.0, 3.42, and 4.0 for the three examples and the reaction was conducted at 40° C. The finished SiH siloxanes were clear liquids having the target structures shown in the Table 2. The SiH content were found to be 0.020%, 0.0240%, and 0.0296% respectively. These siloxanes were made in a silicone carrier fluid to reduce the final viscosity.

TABLE 2

| Example Reference # | 2A |
|---|---|
| [SiH]/[Vi] ratio | 3.00 |
| Component B | VINYL SILOXANE #2 |
| Target structure | |
| % PXL in mixture | 50.0 |
| Carrier fluid type | D5 |
| Wt. % H, theoretical | 0.0200 |
| Cure temp/condition | 40° C. |

| Actual amount | Actual amount |
|---|---|
| MeH-cyclics, g | 5.42 |
| VINYL SILOXANE #2, g | 144.57 |
| D5 carrier fluid | 151.31 |
| Platinum catalyst g | 0.24 |
| Total Batch, g | 301.55 |
| Mixture appearance | Clear, though rubbery liquid |

| Example Reference # | 2B |
|---|---|
| [SiH]/[Vi] ratio | 3.42 |
| Component B | VINYL SILOXANE #2 |
| Target structure | |
| % PXL in mixture | 50.0 |
| Carrier fluid type | D5 |
| Wt. % H, theoretical | 0.0240 |
| Cure temp/condition | 40° C. |

| Actual amount | Actual amount |
|---|---|
| MeH-cyclics, g | 6.15 |
| VINYL SILOXANE #2, g | 143.86 |

TABLE 2-continued

| | |
|---|---|
| D5 carrier fluid | 150.00 |
| Platinum catalyst g | 0.24 |
| Total Batch, g | 300.25 |
| Mixture appearance | Clear, tough rubbery liquid |

| Example Reference # | 2C |
|---|---|
| [SiH]/[Vi] ratio | 4.00 |
| Component B | VINYL SILOXANE #2 |
| Target structure | |
| % PXL in mixture | 50.0 |
| Carrier fluid type | D5 |
| Wt. % H, theoretical | 0.0296 |
| Cure temp/condition | 40° C. |
| Actual amount | Actual amount |
| MeH-cyclics, g | 7.15 |
| VINYL SILOXANE #2, g | 142.87 |
| D5 carrier fluid | 150.00 |
| Platinum catalyst g | 0.24 |
| Total Batch, g | 300.26 |
| Mixture appearance | Clear, thick pourable liquid |

Example 3

Reference

Preparation of an Organohydrogensilaxane Having at Least Two SiH Containing Cyclosiloxane Rings Cyclic SiH-containing siloxanes having branched structures were made by reacting MeH cyclics with dimethylinyl-ended branched silicones or methylinyl cyclics. Illustrated in the Table 3 are the examples derived from VINYL SILOXANE #3 having about 30 dimethylsiloxane repeat on each of the four branches, yielding a total of about 120 dimethylsiloxane units (DP=120) in the presence of the Pt catalyst. The [SiH]/[Vi] ratios were kept at 3.42 and 4.0 for the three examples and the reaction was conducted at 40° C. Separately, a component A) was made using VINYL SILOXANE #4. The SiH siloxanes were clear liquids having the structures summarized in Table 3. The SiH contents were 0.241%, 0.290%, and 0.376% respectively.

TABLE 3

Cyclic SiH siloxane capped, branched organohydrogensiloxanes

| Example Ref # | 3A |
|---|---|
| SiH:Vi ratio | 3.145 |
| Component B | VINYL SILOXANE #3 |

TABLE 3-continued
| Target Structure | |
|---|---|
| | 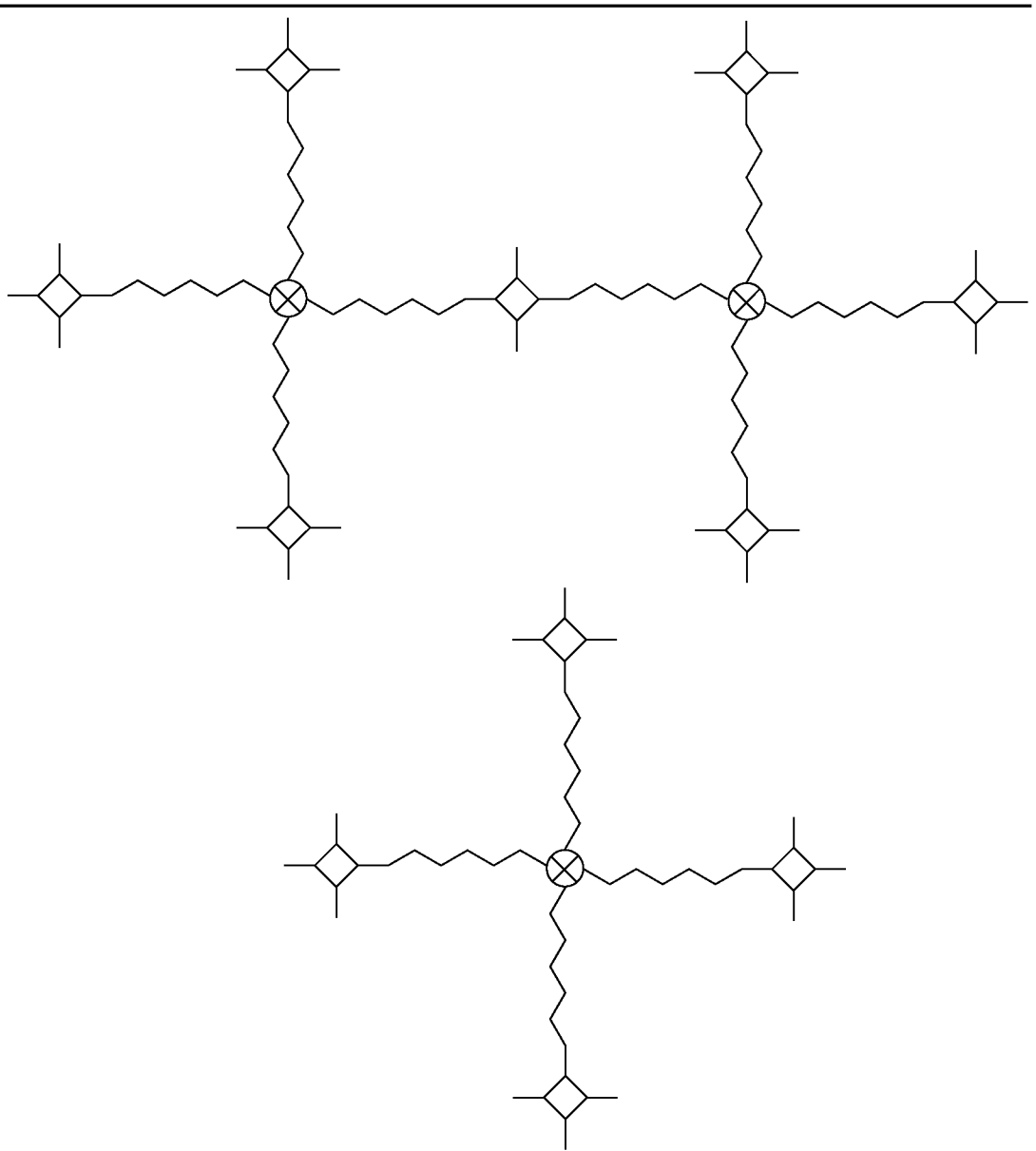 |
| % PXL in mixture | 100.0 |
| Wt. % H, theoretical | 0.241 |
| Actual amount | Actual amount |
|---|---|
| MeH-cyclics, g | 41.156 |
| Vinyl Siloxane #3, g | 158.85 |
| Vinyl Siloxane #4, g | |
| Platinum catalyst, g | 0.160 |
| Total Batch, g | 200.17 |
| Mixture | Clear, viscous liquid |

TABLE 3-continued appearance

| | |
|---|---|
| Example Ref # | 3B |
| SiH:Vi ratio | 4.000 |
| Component B | VINYL SILOXANE #3 |
| Target Structure | |
| % PXL in mixture | 100.0 |
| Wt. % H, theoretical | 0.290 |

| Actual amount | Acutal amount |
|---|---|
| MeH-cyclics, g | 46.563 |
| Vinyl Siloxane #3, g | 153.43 |
| Vinyl Siloxane #4, g | |
| Platinum catalyst, g | 0.160 |
| Total Batch, g | 200.15 |
| Mixture appearance | Clear, viscous liquid |

| | |
|---|---|
| Example Ref # | 3C |
| SiH:Vi ratio | 3.415 |
| Component B | VINYL SILOXANE #4 |
| Target Structure | |

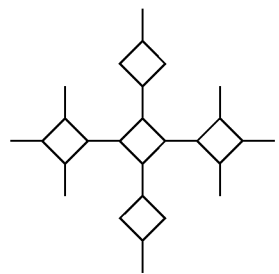

| | |
|---|---|
| % PXL in mixture | 100.0 |
| Wt. % H, theoretical | 0.376 |

| Actual amount | Actual amount |
|---|---|
| MeH-cyclics, g | 64.175 |
| Vinyl Siloxane #3, g | |
| Vinyl Siloxane #4, g | 135.82 |
| Platinum catalyst, g | 0.160 |
| Total Batch, g | 200.16 |
| Mixture appearance | Clear liquid with moderate viscosity |

Example 4

Reference

Preparation of an Organohydrogensilaxane Having at Least Two SiH Containing Cyclosiloxane Rings Organohydrogensiloxanes illustrative as component A) were prepared by mixing MeH CYCLICS, VINYL SILOXANES (as listed in Table 4) or 1, 5 hexadiene, and (if used) D5 as a carrier fluid in a reaction flask. Then, the mixture was catalyzed by the addition of 3-5 ppm of Pt (Pt catalyst solution containing 0.52 wt % Pt). The mixture was heated to 50° C., causing an exothermic hydrosilylation reaction to occur, the temperature was then maintained between 50 and 70° C. for 3 hours. The amounts of MeH CYCLICS and the alkenyl compound were calculated to yield a specific [SiH]/[Vi] ratio of 3.42. The resulting organohydrogensiloxanes were clear liquids having the average structures and properties summarized in Table 4.

TABLE 4

| | Example # | | | |
|---|---|---|---|---|
| | 4A | 4B | 4C | 4D |
| | Amount used for reaction | | | |
| MeH CYCLICS, g | 73.65 | 33.07 | 11.84 | 166.76 |
| Alkenyl compound type | VINYL SILOXANE #1 | VINYL SILOXANE #5 | VINYL SILOXANE #7 | 1,5-Hexadiene |
| Alkenyl compound mass, g | 126.35 | 166.93 | 228.11 | 33.24 |
| D5 Carrier fluid, g | 0 | 0 | 360.7 | 0 |
| Pt catalyst, g | 0.16 | 0.16 | 0.48 | 0.18 |
| Stabilizer, g | 0 | 0 | 3.0 | 0.25 |
| Total batch, g | 200.16 | 200.16 | 604.13 | 200.43 |
| Product appearance | Clear, low viscosity | Clear, low viscosity | Clear, moderate viscosity | Clear, moderate viscosity |
| Wt. % [H] | 0.4319 | 0.1939 | 0.0231 | 0.978 |
| Mn, g/mole | 3,814 | 9,131 | 22,167 | 1,128 |
| Mw, g/mole | 18,688 | 78,303 | 39,103 | 1,591 |

Example 5

Reference

Preparation of A) Organohydrogensiloxanes Having at Least Two SiH Containing Cyclosiloxane Rings Additional examples of the cyclic SiH-bearing siloxanes were made as shown below using component B as listed and MeH CYCLICS as component a).

TABLE 5

Cyclic SiH siloxanes

| Example # | Component B | Comments | Wt. % [H] | Mn, g/mol | Mw, g/mol |
|---|---|---|---|---|---|
| 5A | 1,5-Hexadiene | SiH/diene @ 4.50; as made | 1.06 | 418 | 770 |
| 5B | 1,5-Hexadiene | SiH/diene @ 4.50; VAP stab. | 1.06 | 415 | 760 |
| 5C | Vinyl-siloxane #5 | SiH/vinyl @ 3.42; VAP stab.; made @ 100% solids | 0.4320 | | |
| 5D | Vinyl-siloxane #5 | SiH/vinyl @ 3.42; VAP stab.; made @ 100% solids | 0.1939 | 9114 | 59590 |
| 5E | Vinyl-siloxane #6 | SiH/vinyl @ 3.42; VAP stab.; made @ 80% solids in D5 fluid | 0.1214 | 9721 | 36052 |
| 5F | Vinyl-siloxane #7 | SiH/vinyl @ 3.42; made 40% solids in D5 fluid, VAP stab. | 0.0231 | 14051 | 70697 |
| 5G | Vinyl-siloxane #7 | SiH/vinyl @ 4.0, 40% solids in D5 fluid; VAP stab. | 0.0285 | 26284 | 66219 |
| 5H | Vinyl-siloxane #7 | SiH/vinyl @ 3.42; VAP stab.; made @ 50% solids in D5 fluid | 0.0289 | 29721 | 100166 |
| 5I | Vinyl-siloxane #8 | SiH/vinyl @ 4.0, VAP stab., made 40% solids in D5 fluid | 0.0237 | 44482 | 203232 |
| 5J | Vinyl-siloxane #1 | SiH/vinyl @ 3.42; VAP stab.; made @ 100% solids | 0.4319 | 3658 | 8781 |
| 5K | Vinyl-siloxane #5 | SiH/vinyl @ 3.42; VAP stab.; made @ 100% solids | 0.1939 | 7924 | 21167 |

Example 6

Preparation of Silicone Elastomer Gels from Cyclic SiH Siloxane at Low [SiH]/[Alkenyl] Ratio Silicone elastomer gels were prepared by reacting the organohydrogensiloxane having at least two SiH containing cyclosiloxane rings as component (A) and aliphatic unsaturated compound as component (B) at a low [SiH]/[Alkeny] ratio of 0.36. Cyclic SiH siloxane of Example 5F a 40% solids in D5 fluid where the cyclic SiH-containing siloxane made from MeH-CYCLICS and VINYL SILOXANE #7 at a SiH/alkenyl ratio of 3.42, was reacted with VINYL SILOXANE #2 in D5 fluid and in isodecyl neopentanoate (IDNP) hydrocarbon ester solvent. Table 6 summarizes the reactions and subsequent gels produced.

TABLE 6

Silicone elastomer gels made at low [SiH]/[Alkenyl] ratio and in organic ester

| | Example # | | |
|---|---|---|---|
| | 6A | 6B | 6C |
| [SiH]/[Vi] ratio | 0.361 | 0.361 | 0.361 |
| Component A | 5F | 5F | 5F |
| Comments | SiH/hexenyl @ 3.42; 100 dp siloxane spacer, 40% solids in D5 fluid | SiH/hexenyl @ 3.42; 100 dp siloxane spacer; 40% solids in D5 fluid | SiH/hexenyl @ 3.42; 100 dp siloxane spacer; 40% solids in D5 fluid |
| Wt. % [H] | 0.0231 | 0.0231 | 0.0231 |
| Component B | Vinyl Siloxane #2 | Vinyl Siloxane #2 | Vinyl Siloxane #2 |
| Carrier fluid | D5 fluid | IDNP | IDNP |
| % IEC | 14.6 | 14.6 | 15.9 |
| | Actual amount | Actual amount | Actual amount |
| Example 5F cyclic siloxane, g (40% solids in D5 fluid) | 26.82 | 26.85 | 20.51 |
| Vinyl siloxane #2, g | 33.18 | 33.2 | |
| Vinyl siloxane #9, g | | | 39.52 |
| D5 fluid, g | 240.0 | | |
| IDNP, g | | 240.0 | 240.0 |

TABLE 6-continued

Silicone elastomer gels made at low [SiH]/[Alkenyl] ratio and in organic ester

| | Example # | | |
|---|---|---|---|
| | 6A | 6B | 6C |
| Platinum catalyst g (20 drops give 0.24 g; 4.2 ppm Pt) | 0.24 | 0.24 | 0.24 |
| Total Batch, g | 300.24 | 300.29 | 300.27 |
| Gel appearance | Water-white clear gel; firm ringing | Water-white clear gel | Water-white clear gel |

Example 7

Preparation of Silicone Elastomer Gels

Silicone elastomer gels were made with a low elastomer contents (EC), as illustrated in this example. Silicone elastomer gels (Example 7A and 7C) were made at 3.0% elastomer composition (the total of components (A) and (B)), and 97% D5 fluid (component (D)). The siloxane spacer had an average DP (degree of polymerization) of 100 in these examples.

TABLE 7

Silicone elastomer gels made at low and moderate elastomer contents

| | Example # | | |
|---|---|---|---|
| | 7A | 7B | 7C |
| SiH:Vi ratio | 0.90 | 0.90 | 0.90 |
| Component A) | Example 5F | Example 5G | Example 5G |
| Comment | SiH/vinyl @ 3.415; 100 dp siloxane spacer; 40% solids in D5 fluid | SiH/vinyl @ 4.0; 100 dp siloxane spacer; 40% solids in D5 fluid | SiH/vinyl @ 4.0; 100 dp siloxane spacer; 40% solids in D5 fluid |
| % SiH in A), per FTIR | 0.0231 | 0.0231 | 0.0231 |
| Component B | VINYL SILOXANE #9 | VINYL SILOXANE #9 | VINYL SILOXANE #8 |
| Carrier fluid type | D5 | D5 | D5 |
| % IEC | 3.0 | 20.0 | 3.0 |
| Actual amount | | | |
| Example 5F, g (40% solids) | 10.100 | | |
| Example 5G, g (40% solids; VAP stab) | | 59.39 | 6.70 |
| Vinyl siloxane #2, g | 4.987 | 36.268 | |
| Vinyl siloxane #8, g | | | 6.34 |
| D5 fluid, g | 285.0 | 204.5 | 287.0 |
| Platinum catalyst, g (20 drops give 0.24 g; 4.2 ppm) | 0.24 | 0.24 | 0.24 |
| Total Batch, g | 300.33 | 300.37 | 300.27 |
| Gel appearance | Light straw, clear gel | Light straw, clear gel, firm | Light straw, clear soft gel |

TABLE 8

Silicone elastomer gels made to low elastomer content

| | Example # | | |
|---|---|---|---|
| | 8A | 8B | 8C |
| [SiH]/[Vi] ratio | 0.90 | 0.90 | 0.90 |
| Component A | Example 5C | Example 5D | Example 5D |

Example 8

Silicone Elastomer Gels Made at Low Elastomer Content

Silicone elastomer gels were prepared with low amounts of elastomer content using cyclic SiH-containing siloxanes of relatively short spacer (i.e. low dp). Illustrated below are the silicone elastomer gels made from the SiH siloxane of Example 4C (8 dp spacer) and Example 4D (27dp spacer). All gels in this example had 5 wt % elastomer content (i.e. total of components (A) and (B)), and 95% D5 fluid (component (C)).

TABLE 8-continued

Silicone elastomer gels made to low elastomer content

| | Example # | | |
|---|---|---|---|
| | 8A | 8B | 8C |
| Wt. % [SiH] | 0.430 | 0.190 | 0.190 |
| Component B | Vinyl Siloxane #8 | Vinyl Siloxane #2 | Vinyl Siloxane #8 |
| Carrier fluid type | D5 | D5 | D5 |
| % IEC | 5.0 | 5.0 | 5.0 |

TABLE 8-continued

Silicone elastomer gels made to low elastomer content

| | Example # | | |
|---|---|---|---|
| | 8A | 8B | 8C |
| Actual amount | Actual amount | Actual amount | Actual amount |
| Example 5C siloxane, g | 0.420 | | |
| Example 5D siloxane, g | | 1.351 | 0.902 |
| Vinyl siloxane #2, g | | 13.660 | |
| Vinyl siloxane #8, g | 14.586 | | 14.080 |
| D5 fluid, g | 285.0 | 285 | 285.0 |
| Syl-Off 4000, g (20 drops give 0.24 g; 4.2 ppm) | 0.24 | 0.24 | 0.24 |
| Total Batch, g | 300.25 | 300.25 | 300.22 |
| Gel appearance | Water-white clear gel | Water-white clear gel | Water-white clear gel |

Example 9

Preparation of Silicone Elastomer Blends from Cyclic SiH Siloxanes

Silicone elastomer blends (SEBs) are discrete crosslinked silicone elastomer gel particles dispersed in carrier fluids. SEBs can function effectively as a theological thickener for silicone fluids such as D5 fluid as demonstrated in this example. To make silicone elastomer blends, the elastomer gels of known initial elastomer content (IEC) from several of the above examples were mechanically sheared to obtain small particle size and further diluted to desirable final elastomer content (FEC). For example, sample 9A SEB was made by mechanically shearing an elastomer gel to reduce particle size and then diluted further with D5 fluid to yield a final elastomer content (% FEC) of 10% by weight. The final SEB was a clear thick gel paste with a viscosity of about 676,000 cps. Additional SEBs are shown in Table 9. As illustrated by these examples, extremely high viscosities were observed for these compositions of SEBs in cyclic siloxanes.

TABLE 9

Silicone elastomer blends derived from elastomer gels of cyclic SiH-bearing siloxane

| | Example # | | | | |
|---|---|---|---|---|---|
| Gel composition | 9A | 9B | 9C | 9E | 9F |
| SiH (component (A)) | Example 5E 37 dp | Example 5H 100 dp | Example 5H 100 dp | Example 5H 100 dp | Example 5H 100 dp |
| Vinyl extender (component (B)) | Vinyl siloxane #2 | Vinyl siloxane #2 | Vinyl siloxane #2 | Vinyl siloxane #6 | Vinyl siloxane #7 |
| Carrier fluid (component D) | D5 fluid | D5 fluid | D5 fluid | D5 fluid | D5 fluid |
| % IEC in the elastomer gel | 20 | 20 | 10 | 20 | 20 |
| Dilution fluid | D5 fluid | D5 fluid | D5 fluid | D5 fluid | D5 fluid |
| % FEC in final SEB | 10.0 | 10.0 | 10.0 | 10.0 | 10.0 |
| Viscosity of SEB, cps | 676,000 | 534,950 | 976,150 | 309,750 | 692,400 |

Example 10

Examples of Silicone Elastomer Gels Prepared Neat

Silicone elastomer gels can be prepared without a carrier fluid present, as illustrated in this example. The total of components (A) and (B) represents the elastomer amount and is equal to 100% in these examples.

Silicone elastomer gels were made from the hydrosilylation of the representative cyclic SiH-containing siloxane as component (A) with an alkenyl functional compound in component (B) in the presence of Pt catalyst. The two cyclic SiH siloxanes used for the preparation of 100% silicone elastomer gels were those described above as Example 4J, and example 4K. The molar ratio of silicon-bonded hydrogen [SiH] to [alkenyl] was 0.90. The hardness of these silicone elastomer gels, as measured by Texture Analyzer, is shown in the Tables 10A and 10B.

TABLE 10A

Composition and property and silicone gels of 100% elastomer content

| | Example # | | |
|---|---|---|---|
| | 10A | 10B | 10C |
| Component (A) | Example 5K<br>8 dp PDMS spacer;<br>SiH/Alkenyl @ 3.42 | Example 5K<br>8 dp PDMS spacer;<br>SiH/Alkenyl @ 3.42 | Example 5K<br>8 dp PDMS spacer;<br>SiH/Alkenyl @ 3.42 |
| Component (B) | Vinyl siloxane #2 | Vinyl siloxane #8 | Vinyl-siloxane #10 |
| Component (D): Carrier fluid type | None | None | None |
| [SiH]/[Alkenyl] ratio in gel | 0.90 | 0.90 | 0.90 |
| % Elastomer content | 100.0 | 100.0 | 100.0 |
| Cure temperature | 70° C. | 70° C. | 70° C. |
| Actual amount | | | |
| Component (A), g | 7.98 | 5.41 | 3.19 |
| Component (B), g | 82.07 | 84.73 | 86.89 |
| Pt catalyst, g | 0.07 | 0.07 | 0.07 |
| Total Batch, g | 90.12 | 90.21 | 90.15 |
| Gel appearance | Clear, rigid | Clear, rigid | Clear, rigid |
| Texture Analyzer, Force 1, g of gel | 2617 | 2778 | 1902 |
| Texture Analyzer, Area F-T 1:2, g · sec | 10,959 | 13,434 | 9,904 |
| Gel hardness (compression strength), $N/m^2$ | $2.02 \times 10^5$ | $2.15 \times 10^5$ | $0.147 \times 10^5$ |
| Gel Viscosity as derived from F-T 1:2, $N \cdot s/m^2$ | $84.82 \times 10^5$ | $10.40 \times 10^5$ | $7.66 \times 10^5$ |

TABLE 10B

Composition and property and silicone gels of 100% elastomer content

| | Example # | | |
|---|---|---|---|
| | 10D | 10E | 10F |
| Component (A) | Example 5J<br>27 dp PDMS spacer;<br>SiH/Alkenyl @ 3.42 | Example 5J<br>27 dp PDMS spacer;<br>SiH/Alkenyl @ 3.42 | Example 5J<br>27 dp PDMS spacer;<br>SiH/Alkenyl @ 3.42 |
| Component (B) | Vinyl siloxane #6 | Vinyl siloxane #7 | Vinyl siloxane #2 |
| Component (D): Carrier fluid type | None | None | None |
| [SiH]/[Alkenyl] ratio in gel | 0.90 | 0.90 | 0.90 |
| % IEC | 100.0 | 100.0 | 100.0 |
| Cure temp/condition | 70° C. | 70° C. | 70° C. |
| Actual amount | | | |
| Component (A), g | 11.831 | 4.560 | 3.750 |
| Component (B), g | 78.19 | 85.49 | 86.264 |
| Pt catalyst, g | 0.08 | 0.08 | 0.08 |
| Total Batch, g | 78.27 | 85.567 | 86.344 |
| Gel appearance | Clear, rigid | Clear, rigid | Clear, rigid |
| Texture Analyzer, Force 1, g of gel | 6327 | 4131 | 3590 |
| Texture Analyzer, Area F-T 1:2, g · sec | 33,947 | 21,808 | 19,391 |
| Gel hardness (compression strength), $N/m^2$ | $4.90 \times 10^5$ | $3.20 \times 10^5$ | $2.78 \times 10^5$ |
| Gel Viscosity as derived from F-T 1:2, $N \cdot s/m^2$ | $26.28 \times 10^5$ | $16.88 \times 10^5$ | $15.01 \times 10^5$ |

The silicone elastomer blends were made from the silicone elastomer gels of 100% elastomer content, by grinding/shearing the gels, followed by diluting with the selected carrier fluid, either silicone fluids or organic solvents.

Example 11

Hardness Property of Selected Silicone Elastomers/Gels

A number of silicone elastomer gels were prepared following the procedures described above. These silicone elastomer gels were made from the selected cyclic SiH-containing siloxane as component (A), the alkenyl functional compound in component (B), and the balance quantity of D5 fluid. A trace amount of Pt catalyst at a quantity about 4-10 ppm Pt was used to catalyzed the reaction. The molar ratio of silicon-bonded hydrogen [SiH] to [alkenyl] was varied, as shown in the following table. The hydrosilylation reaction was carried out at 50° C. for 4 hours. Gels formed from 15 minutes to 2 hours after placing in 50° C. water bath, depending on the composition.

The hardness of the silicone elastomer gels derived was characterized using the Texture Analyzer. The "Force 1" is the force reading at the maximum point of the force vs. probe penetration time cure, illustrated in the above figure. This force reading represents the firmness or hardness of the gels in resisting probe penetration. The second property included is the "Force-Time 1:2 Area" reading. This is the area integration between the maximum force reading and the time it elapsed (1 second in this case). This value represents the elastic nature of the silicone elastomer gels. The higher the value, in both properties, the harder the gels is. As illustrated, silicone elastomer gels with a wide range of hardness are produced.

TABLE 11

Gel hardness of various SEBs

| Silicone Elastomer Gel Example # | Component (A): SiH Type & Structure | Component (B) compound | [SiH]/[Alkenyl] ratio in gel | Force 1, g | Force-Time 1:2 Area, g·sec | Gel hardness, N/m2 | Gel viscosity, N·s/m² |
|---|---|---|---|---|---|---|---|
| 11A | 8 dp spacer; SiH/Alkenyl @ 3.42 | 130 dp | 0.80 | 230 | 1249 | $1.78 \times 10^4$ | $9.67 \times 10^4$ |
| 11B | 8 dp spacer; SiH/Alkenyl @ 3.42 | 130 dp | 1.10 | 612 | 2844 | $4.74 \times 10^4$ | $22.01 \times 10^4$ |
| 11C | 8 dp spacer; SiH/Alkenyl @ 3.42 | 130 dp | 1.30 | 600 | 3299 | $4.64 \times 10^4$ | $25.53 \times 10^4$ |
| 11D | 8 dp spacer; SiH/Alkenyl @ 3.42 | 200 dp | 1.00 | 242 | 1307 | $1.87 \times 10^4$ | $10.12 \times 10^4$ |
| 11E | Q-branched, 120 dp total; @ 3.42 | 200 dp | 0.95 | 149 | 806 | $1.15 \times 10^4$ | $6.24 \times 10^4$ |
| 11F | C6 organic spacer; SiH/Alkenyl @ 3.42 | 130 dp | 0.85 | 142 | 746 | $1.10 \times 10^4$ | $5.77 \times 10^4$ |
| 11G | C6 organic spacer; SiH/Alkenyl @ 3.42 | 130 dp | 1.00 | 391 | 1919 | $3.03 \times 10^4$ | $14.85 \times 10^4$ |
| 11H | C6 organic spacer; SiH/Alkenyl @ 3.0 | 200 dp | 0.90 | 112 | 612 | $0.867 \times 10^4$ | $4.74 \times 10^4$ |
| 11I | C6 organic spacer; SiH/Alkenyl @ 4.0 | 200 dp | 1.00 | 145 | 785 | $1.12 \times 10^4$ | $6.08 \times 10^4$ |
| 11J | C6 organic spacer; SiH/Alkenyl @ 3.0 | 220 dp; Q-branched | 1.00 | 562 | 2671 | $4.35 \times 10^4$ | $20.67 \times 10^4$ |
| 11H | with mixed (C6 organic/8 dp @ 50/50) @ 3.42 | 200 dp | 0.95 | 59 | 318 | $0.457 \times 10^4$ | $2.46 \times 10^4$ |

Example 12

Silicone Gels Hardness Measured by the Texture Analyzer

Elastomer gels with very low hardness (soft gels) and with very high hardness readings (not shown yet) can be conveniently prepared by controlling the % elastomer content. The total of components (A) and (B) represents the elastomer content and can be as high as 100%. In the case of neat elastomers, the hardness of such gels is very high and can be processed into powdery type products to give a powdery feel.

Illustrated in the Table 12, gels were prepared from various component (A) and alkenyl-functional compound in component (B) to 10 and 20% elastomer content. Dow Corning 245 fluid was used as component (D). Very soft gels with a force of 4 g were produced. On the other hand, gels with very high force readings may be produced from these components by raising the wt. % elastomer content.

TABLE 12

Silicone gels with different hardness

| Silicone Elastomer Gel Example # | Component (A): SiH Type & Structure | Component (B): dp of Alkenyl Compound | Wt. % Elastomer; (A) + (B) | Force 1, g | Force-Time 1:2 Area, g·sec | Gel hardness, N/m2 | Gel viscosity, N·s/m² |
|---|---|---|---|---|---|---|---|
| 12A | 27 dp; made 80% solids in D5 fluid | 130 dp | 20.0 | 161 | 864 | $1.24 \times 10^4$ | $6.69 \times 10^4$ |
| 12B | 27 dp; made 80% solids in D5 fluid | 200 dp | 20.0 | 106 | 582 | $0.82 \times 10^4$ | $4.50 \times 10^4$ |
| 12C | 37 dp; made 80% solids in D5 fluid | 37 dp | 20.0 | 46 | 263 | $0.356 \times 10^4$ | $2.04 \times 10^4$ |
| 12D | 37 dp; made 80% solids in D5 fluid | 37 dp | 10.0 | 4 | 30 | $0.031 \times 10^4$ | $0.232 \times 10^4$ |
| 12E | 37 dp; made 80% solids in D5 fluid | 130 dp | 20.0 | 192 | 1037 | $1.49 \times 10^4$ | $8.03 \times 10^4$ |
| 12F | 100 dp; made 50% solids in D5 fluid | 130 dp | 20.0 | 139 | 780 | $1.08 \times 10^4$ | $6.04 \times 10^4$ |
| 12G | 100 dp; made 50% solids in D5 fluid | 130 dp | 10.0 | 29 | 171 | $0.224 \times 10^4$ | $1.32 \times 10^4$ |
| 12H | 100 dp; made 50% solids in D5 fluid | 100 dp | 20.0 | 194 | 1054 | $1.50 \times 10^4$ | $8.16 \times 10^4$ |
| 12I | 100 dp; made 50% solids in D5 fluid | 100 dp | 10.0 | 38 | 221 | $0.294 \times 10^4$ | $1.71 \times 10^4$ |
| 12J | 100 dp; made 50% solids in D5 fluid | 37 dp | 20.0 | 254 | 1403 | $1.97 \times 10^4$ | $10.86 \times 10^4$ |
| 12K | 130 dp; made 50% solids in D5 fluid | 200 dp | 20.0 | 101 | 565 | $0.782 \times 10^4$ | $4.37 \times 10^4$ |

The actual force vs. probe penetration time cures obtained from Texture Analyzer for a selected group of gels from Table 12 are shown in FIG. 1.

Example 13

Additional Examples of SEBs Made at Low SiH/Vinyl Ratios

Elastomers and gels may be formed over a wide range of SiH/vinyl ratios and at relatively low SiH/vinyl ratios. To illustrate this, the following examples were prepared.

Component (A) in this example was an organohydrogensiloxane similar to Example 5F with a 27dp siloxane spacer, made from MeH cyclics and VINYL SILOXANE #5 using a SiH/vinyl ratio of 3.4.

| | Example # | | | | | |
|---|---|---|---|---|---|---|
| | 13A | 13B | 13C | 13D | 13E | 13F |
| SiH:Vi ratio | 0.90 | 0.70 | 0.50 | 0.30 | 0.20 | 0.15 |
| Component (B): | VINYL SILOXANE #7 | VINYL SILOXANE #7 | VINYL SILOXANE #7 | VINYL SILOXANE #7 | VINYL SILOXANE #7 | VINYL SILOXANE #7 |
| Component (D): Carrier fluid type Actual amount | None | None | None | None | None | None |
| Component (A): grams | 8.41 | 6.70 | 4.90 | 3.01 | 2.03 | 1.54 |
| Component (B): grams | 71.594 | 73.303 | 75.10 | 76.99 | 77.97 | 78.46 |
| Syl-Off 4000, g (0.052% Pt) | 0.05 | 0.05 | 0.05 | 0.05 | 0.05 | 0.05 |
| Total Batch, g | 80.052 | 80.057 | 80.051 | 80.053 | 80.056 | 80.052 |
| Gel/mixture appearance | Clear solid gel | Clear solid gel | Clear solid gel | Clear solid gel | Clear solid gel | Clear pourable liquid; no gel formed |

-continued

| | Example # | | | | | |
|---|---|---|---|---|---|---|
| | 13A | 13B | 13C | 13D | 13E | 13F |
| Texture Analyzer, Force 1, g of gel | 3349 | 1749 | 491 | 44.3 | 3.0 | |
| Texture Analyzer, Area F-T 1:2, g · sec | 18,036 | 9,136 | 2,548 | 243 | 23.4 | |
| Gel hardness (compression strength), N/m2 | $25.9 \times 10^4$ | $13.5 \times 10^4$ | $3.80 \times 10^4$ | $0.343 \times 10^4$ | $0.023 \times 10^4$ | |
| Gel Viscosity as derived from F-T 1:2, N · s/m2 | $13.96 \times 10^5$ | $7.07 \times 10^5$ | $1.97 \times 10^5$ | $0.188 \times 10^5$ | $0.018 \times 10^5$ | |

Preparation: prescribed amounts of components (A) and (B) are charged to a reaction container and mixed to homogeneous, then about 3.5 ppm of Pt catalyst (i.e. 0.05 g of Dow Corning Syl-Off Pt solution @ 0.52% Pt by weight) was introduced while under stirring. The hydrosilylation reaction was carried out at 70° C. for 3 hrs. All mixtures except Example 13F gelled within 30 minutes of heating. The gel hardness was characterized using a Texture Analyzer.

Example 14

Comparative Example

Comparison Examples: Silicone Elastomer Gels from Linear MeH Siloxane/Hexadiene Chemistry The thickening or gelling capabilities of representative SEBs of the present invention were evaluated vs thickening capabilities of known silicone elastomers known in the art for thickening such as those described in U.S. Pat. Nos. 5,811,487 and 5,880,210. Two silicone elastomer blend compositions were prepared using $MD_{94}D'_6M$ SiH polymer (MeH Linear) and 1,5-hexadiene as chain extender, and amount of D5 fluid as the carrier fluid to provide elastomer content of 10.0 and 5.0% by weight. A water-white, weak and soft gel was obtained for Example 8A, but was not as firm as Example 6A as described above. No gel or elastomer was formed in the Example 8B composition, at 5.0% elastomer content. This example demonstrates the improved thickening and gel-forming capacity of the cyclic SiH-containing siloxane based composition of the present invention vs conventional linear siloxane based silicone elastomers of the art.

TABLE 8

Comparison silicone elastomer gels

| | Example # | |
|---|---|---|
| | 8A | 8B |
| [SiH]/[Vi] ratio | 0.90 | 0.90 |
| Organohydrogensiloxane | MeH Linear | MeH Linear |
| % SiH in SiH Polymer | 0.068 | 0.068 |
| Vinyl compound | 1,5-Hexadiene | 1,5-Hexadiene |
| Carrier fluid type | D5 | D5 |
| % IEC | 10.0 | 5.0 |
| Cure temp/condition | 50° C. | 50° C. |
| Actual amount | | |
| MeH Linear, g | 29.14 | 14.581 |
| 1,5-Hexadiene, g | 0.88 | 0.433 |
| D5 fluid, g | 285.0 | 285.0 |
| Platinum catalyst, g (20 drops give 0.24 g; 4.2 ppm) | 0.24 | 0.24 |
| Total Batch, g | 315.26 | 300.25 |
| Gel appearance | Water-white, very soft gel | Water-white clear liquid, low viscosity |

Example 15

Preparation of Silicone Elastomer Gels Containing Actives

Silicone Elastomer gels were prepared from cyclic SiH-containing siloxane having various chain architectures (component A), as well as aliphatic unsaturated compounds of various structure and type in component (B). The amounts and components (A) and (B) were calculated to yield a pre-determined [SiH]/[Alkeny] molar ratio and a pre-determined % elastomer content in the cured gel. Examples 15B and 15D were charged with 7.15 wt % VAP during the formation of the silicone elastomer gel, and is representative of the "pre-load method".

TABLE 15

| | Example # | | | |
|---|---|---|---|---|
| | 15A | 15B | 15C | 15D |
| Component (A): reference | 4A | 4A | 4B | 4B |
| Component (B): Alkenyl Compound | VINYL SILOXANE #2 | VINYL SILOXANE #2 | VINYL SILOXANE #2 | VINYL SILOXANE #2 |
| [SiH]/[Alkenyl] mol. ratio | 0.90 | 1.00 | 0.90 | 1.00 |
| Component (C): Carrier fluid | D5 | D5 | D5 | D5 |

TABLE 15-continued

|  | Example # | | | |
|---|---|---|---|---|
|  | 15A | 15B | 15C | 15D |
| Component (E): Wt. % VAP in gel | 0.0 | 7.15 | 0.0 | 7.15 |
| Gel appearance | Clear | Clear, bright yellow | Clear | Clear, bright yellow |
| Wt. % IEC in gel | 20 | 20 | 20 | 20 |
| Vitamin Loading Method |  | Pre-load |  | Pre-load |
| Texture analyzer, Force 1, g | 143 | 120 | 171 | 135 |
| Texture analyzer, force-time 1-2, g · sec | 780 | 659 | 935 | 734 |
| Gel hardness, N/m$^2$ | 11,068 | 9,288 | 13,236 | 10,449 |
| Viscosity of gel, N · s/m$^2$ | 60,373 | 51,088 | 72,371 | 56,813 |

The silicone elastomer gels in these examples were prepared according to the following procedures:
1) charge all components except catalyst to a glass container (or a reactor) and stir to homogeneous;
2) catalyze the reaction mixture (with 3-5 ppm Pt) and quickly place the mixture in a 70° C. water bath and continue the stirring until the mixture gelled, record the time it takes to reach the gel state;
3) leave the reaction mixture container in the 70° C. water bath for a total of 4 hrs.

Example 16

Preparation of Silicone Elastomer Gels Containing Actives

Silicone elastomer gels with and without a vitamin active were also derived from organohydrogencyclosiloxanes of varying molecular structure as shown in the examples summarized in Table 16. The hardness of the VAP active containing silicone elastomer gels was characterized by the Texture Analyzer, as described above. The gels were prepared according to the procedure described in Example 15.

TABLE 16

|  | Example # | | | |
|---|---|---|---|---|
|  | 16A | 16B | 16C | 16D |
| Component (A): Reference | 4C | 4C | 4D | 4D |
| Component (B): Alkenyl Compound | VINYL SILOXANE #2 | VINYL SILOXANE #2 | VINYL SILOXANE #2 | VINYL SILOXANE #2 |
| [SiH]/[Alkenyl] mol. ratio | 0.85 | 1.00 | 0.85 | 1.00 |
| Component (C): Carrier fluid | D5 | D5 | D5 | D5 |
| Component (E): Wt. % VAP in gel | 0.0 | 7.15 | 0.0 | 7.15 |
| Gel appearance | Clear, firm gel | Clear, bright yellow firm gel | Clear, firm gel | Clear, bright yellow, firm gel |
| Wt. % IEC in gel | 20 | 20 | 20 | 20 |
| Vitamin Loading Method |  | Pre-load |  | Pre-load |
| Texture analyzer, Force 1, g | 108 | 106 | 127 | 111 |
| Texture analyzer, force-time 1-2, g · sec | 590 | 582 | 633 | 609 |
| Gel hardness, N/m$^2$ | 8,359 | 8,205 | 9,830 | 8,592 |
| Viscosity of gel, N · s/m$^2$ | 45,667 | 45,048 | 48,995 | 47,138 |

Example 17

Preparation of Silicone Elastomer Gels

Silicone elastomer gels with and without a vitamin active were also derived from organohydrogencyclosiloxanes having an organic spacer as shown in the examples summarized in Table 17. The gels were prepared according to the procedure described in Example 15.

TABLE 17

| | Example # | |
|---|---|---|
| | 17A | 17B |
| Component (A): reference e | 4D | 4D |
| Component (B): Alkenyl Compound | Vinyl siloxane #2 | Vinyl siloxane #2 |
| Component (C): Carrier fluid | D5 fluid | D5 fluid |
| [SiH]/[Alkenyl] mol. Ratio in gel | 0.85 | 1.00 |

TABLE 17-continued

| | Example # | |
|---|---|---|
| | 17A | 17B |
| Component (D): vitamin active % | 0.00 | 7.15 |
| Silicone gel appearance | Clear, yellowish gel | Clear, yellowish gel |
| % Elastomer in Gel | 20.0 | 20.0 |
| Vitamin Loading Method | | Pre-load |
| Texture analyzer, Force 1, g | 142.0 | 103.5 |
| Texture analyzer, force-time 1-2, g · sec | 746 | 566 |
| Gel hardness, N/m$^2$ | 10,991 | 8,011 |
| Viscosity of gel, N · s/m$^2$ | 57,742 | 43,809 |

Example 18

Preparation of Silicone Elastomer Gels Containing Actives

Additional examples of silicone elastomer gels prepared from various organohydrogencyclosiloxanes using the Example 3 procedures are summarized Table 18.

TABLE 18

| | Example # | | | |
|---|---|---|---|---|
| | 18A | 18B | 18C | 18D |
| Component (A): reference | 4A | 4A | 4B | 4B |
| Component (B): Alkenyl Compound | VINYL SILOXANE #2 | VINYL SILOXANE #2 | VINYL SILOXANE #2 | VINYL SILOXANE #2 |
| Component (C): Carrier fluid | D5 | D5 | D5 | D5 |
| [SiH]/[Alkenyl] mol. Ratio in gel | 0.90 | 1.00 | 0.90 | 1.00 |
| Component (E): vitamin active % | 0.00 | 7.15 | 0.00 | 7.15 |
| Silicone gel apparance | Clear, yellowish gel | Clear, yellowish gel | Clear, yellowish gel | Clear, yellowish gel |
| % Elastomer in Gel | 20.0 | 20.0 | 20.0 | 20.0 |
| Vitamin Loading Method | | Pre-load | | Pre-load |
| Texture analyzer, Force 1, g | | | 130.6 | 148.0 |
| Texture analyzer, force-time 1-2, g · sec | | | 711 | 803 |
| Gel hardness, N/m$^2$ | | | 10,109 | 11,455 |
| Viscosity of gel, N · s/m$^2$ | | | 55,033 | 62,154 |

Example 19

Preparation of Silicone Elastomer Blends Containing Actives

Silicone elastomer blends were prepared from several of the silicone elastomer gels by mechanically shearing a silicone elastomer gel composition characterized as having an initial elastomer content (IEC) to reduce particle size, and subsequently diluting the mixture with additional carrier fluid to a desired final elastomer content (FEC). Various silicone elastomer blends, as summarized in Table 19, were made by mechanically shearing silicone gel compositions using a Hauschild mixer to reduced particle size and then diluted further with Dow Corning 245 fluid to yield silicone elastomer blends having a final elastomer content (FEC) of 10% by weight. The silicone blend compositions of these examples contained VAP, which can be included using the pre-load method (Example 19B and 19D), or from post-loading the VAP by its addition to a silicone gel composition (Example 19A and 19C).

TABLE 19

| | Example # | | | |
|---|---|---|---|---|
| | 19A | 19B | 19C | 19D |
| Gel Example # reference | 15A | 15B | 15C | 15D |
| Component (C): Carrier fluid | D5 fluid | D5 fluid | D5 fluid | D5 fluid |
| Component (E): Wt. % VAP in SEB | 3.53 | 3.58 | 3.53 | 3.58 |
| Vitamin Loading Method | Post-load | Pre-load | Post-load | Pre-load |
| Wt. % Elastomer Content in SEB | 10.0 | 10.0 | 10.0 | 10.0 |
| SEB appearance | Clear bright yellowish, smooth gel | Clear bright yellowish, smooth gel | Clear bright yellowish, smooth gel | Clear bright yellowish, smooth gel |
| Viscosity of SEB (@ 10% FEC), cps | 255,000 | 342,000 | 227,000 | 677,000 |

Example 20

Preparation of Silicone Elastomer Blends Containing Actives

Additional examples of silicone elastomer blends, prepared from various silicone elastomer gels using the Example 7 procedures, are summarized Table 20.

TABLE 20

| | Example # | | | |
|---|---|---|---|---|
| | 20A | 20B | 20C | 20D |
| Gel Example # reference | 16A | 16B | 16C | 16D |
| Component (C): Carrier fluid | D5 fluid | D5 fluid | D5 fluid | D5 fluid |
| Component (E): Wt. % VAP in SEB | 3.53 | 3.58 | 3.53 | 3.58 |
| Vitamin Loading Method | Post-load | Pre-load | Post-load | Pre-load |
| Wt. % Elastomer Content in SEB | 10.0 | 10.0 | 10.0 | 10.0 |
| SEB appearance | Clear bright yellowish, smooth gel | Clear bright yellowish, smooth gel | Clear bright yellowish, smooth gel | Clear bright yellowish, smooth gel |
| Viscosity of SEB (@ 10% FEC), cps | 295,000 | 1,220,000 | 43,800 | 364,000 |

Example 21

Preparation of Silicone Elastomer Blends Containing Actives

Additional examples of silicone elastomer blends, prepared from various silicone elastomer gels using the Example 19 procedures, are summarized Table 21.

High-performance liquid chromatography (HPLC) was used to verify the presence and integrity of VAP active in SEBs. The details of the HPLC analysis techniques are summarized below.

HPLC Assays for Vitamin A Palmitate in SEB

Standard Preparation

Standards were prepared by creating a stock solution of 1000 ug/ml VAP in hexane. This was done by measuring 107.2 mg VAP into a 100 ml volumetric flask. The flask was then filled to the 100 ml level with hexane. The stock solution was then diluted into solutions with concentration of 4, 40, 100, 300, and 500 ug/ml. A calibration curve was constructed using all standards from 4 to 1000 ug/ml.

SEB Sample Extraction

There were two methods of sample extraction used in this study. PXL SEB samples were extracted using hexane only. This was done by adding 0.5 g SEB to 20 g hexane in a vial. The formulation samples (Sepigel and body lotions) were extracted by adding 1 g of formulation sample with 10 g THF:IPA (1:1). The samples were then put on a wrist action shaker for 2 hours of mixing. After mixing was complete the samples were filtered into HPLC vials using 0.45 micron PTFE filters.

HPLC Conditions

The assays of VAP in this invention were performed on one of the two HPLC systems: a Waters 600E HPLC equipped with a Waters 991 PDA detector or Waters 2695 Separations unit equipped with a Waters 2996 PDA detector. The column and column guard were Novapak C18 from Waters. The column was heated to a constant temperature of 35° C. The mobile phase was 45% methanol, 20% acrylnitrile, and 35% isopropanol set at a flow rate of 1 ml/min. 10 ul of each sample were injected and allowed to run for 12 minutes. The PDA detector was set to 325 nm wavelength.

TABLE 21

| | Example # | | | |
|---|---|---|---|---|
| | 21A | 21B | 21C | 21D |
| Gel Example # reference | 16A | 16B | 16C | 16D |
| Component (C): Carrier fluid | D5 fluid | D5 fluid | D5 fluid | D5 fluid |
| % Elastomer in Gel | 20.0 | 20.0 | 20.0 | 20.0 |
| Composition of silicone elastomer blend | | | | |
| Silicone Gel, g | 50.00 | 50.00 | 50.02 | 50.03 |
| VAP active, g | 3.69 | 0 | 3.57 | 0 |
| D5 fluid, g | 46.34 | 50.0 | 46.45 | 50.03 |
| Batch total, g | 100.03 | 100.0 | 100.04 | 100.06 |
| Vitamin Loading Method | Post-load | Pre-load | Post-load | Pre-load |

TABLE 21-continued

|  | 21A | 21B | 21C | 21D |
|---|---|---|---|---|
| Wt. % VAP in SEB, as formulated | 3.69 | 3.57 | 3.57 | 3.58 |
| Wt. % VAP in SEB, per HPLC | 3.29 | 3.57 | 3.36 | 3.39 |
| SEB Appearance as prepared | Clear, yellowish gel | Clear, yellowish gel | Clear, yellowish gel | Clear, yellowish gel |
| Wt. % Elastomer in SEB | 10.0 | 10.0 | 10.0 | 10.0 |
| Viscosity of SEB, cps | 183,000 | 412,000 | 194,000 | 515,000 |

Example # shown above for Example 21.

Example 22

Preparation of Silicone Elastomer Blends Containing Actives

Additional examples of silicone elastomer blends, prepared from various silicone elastomer gels using the Example 19 procedures, are summarized Table 22.

High-performance liquid chromatography (HPLC) was used to verify the presence and integrity of VAP active in SEBs using the procedures as summarized in Example 21.

TABLE 22

|  | 22A | 22B |
|---|---|---|
| Gel Example # reference | 17A | 17B |
| Component (C): Carrier fluid | D5 fluid | D5 fluid |
| % Elastomer in Gel | 20.0 | 20.0 |
| Composition of silicone elastomer blend | | |
| Silicone Gel, g | 50.04 | 50.05 |
| VAP active, g | 3.57 | 0 |

TABLE 22-continued

|  | 22A | 22B |
|---|---|---|
| D5 fluid, g | 46.47 | 50.05 |
| Batch total, g | 100.08 | 100.1 |
| Vitamin Loading Method | Post-load | Pre-load |
| Wt. % VAP in SEB, as formulated | 3.57 | 3.58 |
| Wt. % VAP in SEB, per HPLC | 3.39 | 3.31 |
| SEB Appearance as prepared | Clear, yellowish gel | Clear, yellowish gel |
| Wt. % Elastomer in SEB | 10.0 | 10.0 |
| Viscosity of SEB, cps | 352,000 | 612,000 |

Example 23

Preparation of Silicone Elastomer Gels Containing Actives without Carrier Fluids Silicone elastomer gels were prepared without adding any carrier fluid (component C) from various organohydrogencyclosiloxanes using Example 15 procedures. The formulations and resulting gel properties are summarized Table 23.

TABLE 11A

|  | 23A | 23B | 23C |
|---|---|---|---|
| Component (A): reference | 4A | 4A | 4A |
| Component (B): Alkenyl extender type | VINYL SILOXANE #2 | VINYL SILOXANE #8 | VINYL SILOXANE #10 |
| Component (C): Carrier fluid type | None | None | None |
| Component (E): Active type and wt. % | Vitamin A Palmitate; 5% | Vitamin A Palmitate; 5% | Vitamin A Palmitate; 5% |
| [SiH]/[Alkenyl] ratio in gel | 0.95 | 0.95 | 0.95 |
| % Elastomer content | 95.0 | 95.0 | 95.0 |
| Cure temp/condition | 70° C. | 70° C. | 70° C. |
| Actual amount | | | |
| Component (A), SiH, g | 7.99 | 5.29 | 3.16 |
| Component (B), alkenyl extender, g | 77.58 | 80.23 | 82.37 |
| Component (D): Pt catalyst (0.52%; Syl-Off 4000), g | 0.068 | 0.068 | 0.068 |
| Component (E): Vitamin A Palmitate/BHT mixture of 98.5/1.5, g | 4.57 | 4.55 | 4.57 |
| Total Batch, g | 90.21 | 90.14 | 90.17 |
| Gel appearance | Light yellowish, milky | Light yellowish, milky | Light yellowish, milky |
| Texture Analyzer, Force 1, g of gel | 2916 | 1660 | 1330 |
| Texture Analyzer, Area F-T 1:2, g · sec | 15,847 | 8,974 | 7,233 |

TABLE 11A-continued

| | Example # | | |
|---|---|---|---|
| | 23A | 23B | 23C |
| Gel hardness, N/m² | 225,704 | 128,487 | 102,944 |
| Viscosity of gel, N · s/m² | 1,226,586 | 694,604 | 559,847 |

TABLE 23B

| | Example # | | |
|---|---|---|---|
| | 23D | 23E | 23F |
| Component (A): SiH PXL type and structure | 4B | 4B | 4B |
| Component (B): Alkenyl extender type | Vinyl Siloxane #6 | Vinyl Siloxane #7 | Vinyl Siloxane #2 |
| Component (C): Carrier fluid type | None | None | None |
| Component (E): Active type and wt. % | Vitamin A Palmitate; 5% | Vitamin A Palmitate; 5% | Vitamin A Palmitate; 5% |
| [SiH]/[Alkenyl] ratio in gel | 0.90 | 0.90 | 0.90 |
| % IEC | 100.0 | 100.0 | 100.0 |
| Cure temp/condition | 70° C. | 70° C. | 70° C. |
| Actual amount | | | |
| Component (A), SiH PXL, g | 11.776 | 4.510 | 3.755 |
| Component (B), alkenyl extender, g | 73.14 | 80.99 | 81.77 |
| Component (D): Pt catalyst (0.52%; Syl-Off 4000), g | 0.068 | 0.068 | 0.068 |
| Component (E): Vitamin A Palmitate/BHT mixture of 98.5/1.5, g | 4.57 | 4.58 | 4.56 |
| Total Batch, g | 89.55 | 90.15 | 90.15 |
| Gel appearance | Almost clear, yellowish, firm gel | Hazy to opaque yellowish, firm gel | Milky opaque, light yellowish gel |
| Texture Analyzer, Force 1, g of gel | 5,667 | 2,744 | 3,658 |
| Texture Analyzer, Area F-T 1:2, g · sec | 30,940 | 14,847 | 19,835 |
| Gel hardness, N/m² | 438,636 | 212,390 | 283,136 |
| Viscosity of gel, N · s/m² | 2,394,811 | 1,149,184 | 1,535,264 |

The invention claimed is:

1. A gel composition comprising a silicone elastomer from the reaction of:
   A) an organohydrogensiloxane prepared by a hydrosilylation reaction of
      a) an organohydrogencyclosiloxane having at least two SiH units on the siloxane ring and,
   B) a compound or mixture of compounds containing at least two aliphatic unsaturated groups in its molecule, wherein the molar ratio of SiH units to unsaturated group ranges from 2/1 to 8/1
   B²) an organovolysiloxane comprising at least two siloxane units having a formula $R^2R_mSiO_{(4-m)/2}$ wherein R is an organic group, $R^2$ is a monovalent unsaturated aliphatic group, and m is zero to 3,
   C) a hydrosilylation catalyst, and;
   D) carrier fluid selected from decamethylcyclopentasiloxane, isododecane, or isodecyl neopentanoate.

2. The composition of claim 1 further comprising
   E) a personal care or healthcare active.

3. The composition of claim 1 wherein the organohydrogencyclosiloxane has the formula $[(CH_3)HSiO]_g$ where g is 3-8.

4. The composition of claim 1 wherein B) the compound containing at least two aliphatic unsaturated groups in its molecule is selected from a compound having the formula $R^2$—Y—$R^2$ where $R^2$ is a monovalent unsaturated aliphatic group and Y is a divalent hydrocarbon, a siloxane, a polyoxyalkylene or mixtures thereof.

5. The composition of claim 1 wherein the organopolysiloxane $B^2$ has the formula $(R_2R^2SiO_{0.5})(SiO_2)_w(R_2R^2SiO_{0.5})$ $(R_2R^2SiO_{0.5})(SiO_2)_w(R_2SiO)_x(R_2R^2SiO_{0.5})$, $(R_2R^2SiO_{0.5})(R_2SiO)_x(R_2R^2SiO_{0.5})$, $(R_3SiO_{0.5})(R_2SiO)_x(R_2RSiO)_y(R_3SiO_{0.5})$, $(R_3SiO_{0.5})(R_2SiO)_x(R_2RSiO)_y(RSiO_{1.5})_z(R_3SiO_{0.5})$, or $(R_3SiO_{0.5})(R_2SiO)_x(R_2RSiO)_y(SiO_2)_w(R_3SiO_{0.5})$, where w≧0, x≧0, y≧2, and z is ≧0, and R is an organic group, $R^2$ is a monovalent unsaturated aliphatic group.

6. The composition of claim 5 wherein R is methyl and $R^2$ is $CH_2=CH-$ or $CH_2=CH-(CH_2)_4-$.

7. The composition of claim 6 wherein the organopolysiloxane $B^2$ is a vinyl functional or hexenyl functional polydimethylsiloxane having the average formula;

$CH_2=CH(Me)_2SiO[Me_2SiO]_xSi(Me)_2CH=CH_2$, $CH_2=CH-(CH_2)_4-(Me)_2SiO[Me_2SiO]_xSi(Me)_2-(CH_2)_4-CH=CH_2$, or $Me_3SiO[(Me)_2SiO]_x[CH_2=CH(Me)SiO]_ySiMe_3$ wherein Me is methyl, $x \geq 0$, and $y \geq 2$.

8. The composition of claim 1 wherein C) the hydrosilylation catalyst is a platinum group containing catalyst.

9. The composition of claim 1 wherein the molar ratio of A)/$B^2$) is from 10/1 to 1/10.

10. The composition of claim 2 wherein E) is a personal care active selected from a vitamin, sunscreen, plant extract, or fragrance.

11. The composition of claim 2 wherein E) is a health care active selected from a topical drug active, protein, enzyme, antifugual, or antimicrobial agent.

12. The composition of claim 2 wherein component E) is vitamin A palmitate.

13. The composition of claim 2 wherein component E) is octyl methoxycinnamate.

14. A process for preparing a silicone elastomer gel comprising:
I) reacting;
   a) an organohydrogencyclosiloxane having at least two SiH units on a siloxane ring,
   B) a compound or mixture of compounds containing at least two aliphatic unsaturated groups in its molecules,
   C) a hydrosilylation catalyst
to form
   A) an organohydrogensiloxane having at least two SiH containing cyclosiloxane rings in its molecule,
   wherein the molar ratio of the SiH units of component a) to the aliphatic unsaturated groups of component B) ranges from 2/1 to 8/1,
II) further reacting;
   A) the organohydrogensiloxane having at least two SiH containing cyclosiloxane rings in its molecule, with additional quantities of
   B) the compound or mixture of compounds containing at least two aliphatic unsaturated groups in its molecules, —
   C) the hydrosilylation catalyst,
in the presence of
   D) carrier fluid, selected from decamethylcyclopentasiloxane, isododecane, or isodecyl neopentanoate,
to form the silicone elastomer gel.

15. A process for preparing a silicone elastomer gel containing an active comprising:
I) reacting;
   a) an urganohydrogencyclosiloxane having at least two SiH units on a siloxane ring,
   B) a compound containing at least two aliphatic unsaturated groups in its molecules,
   C) a hydrosilylation catalyst
to form
   A) an organohydrogensiloxane having at least two SiH containing cyclosiloxane rings in its molecule,
   wherein the molar ratio of the SiH units of component a) to the aliphatic unsaturated groups of component B) ranges from 2/1 to 8/1,
II) further reacting;
   A) the organohydrogensiloxane having at least two SiH containing cyclosiloxane rings in its molecule, with additional quantities of
   B) the compound containing at least two aliphatic unsaturated groups in its molecules,
   C) the hydrosilylation catalyst,
in the presence of
   D) an optional carrier fluid
to form a silicone elastomer gel,
II) admixing
   E) a personal care or healthcare active with the silicone elastomer gel to form the silicone elastomer gel containing active.

16. A process for preparing a silicone elastomer gel containing an active comprising:
I) reacting;
   a) an organohydrogencyclosiloxane having at least two SiH units on a siloxane ring,
   B) a compound containing at least two aliphatic unsaturated groups in its molecules,
   C) a hydrosilylation catalyst
to form
   A) an organohydrogensiloxane having at least two SiH containing cyclosiloxane rings in its molecule,
   wherein the molar ratio of the SiH units of component a) to the aliphatic unsaturated groups of component B) ranges from 2/1 to 8/1,
II) further reacting;
   A) the organohydrogensiloxane having at least two SiH containing cyclosiloxane rings in its molecule, with additional quantities of
   B) the compound containing at least two aliphatic unsaturated groups in its molecules,
   C) the hydrosilylation catalyst,
in the presence of
   D) an optional carrier fluid,
   E) a personal care or healthcare active
to form the silicone elastomer gel containing active.

17. The silicone elastomer gel prepared according to claim 14.

18. A process for preparing a gel paste composition comprising;
I) shearing the silicone elastomer gel of claim 1,
II) combining the sheared silicone elastomer gel with additional quantities of
   D) the carrier fluid to form a gel paste composition.

19. The gel paste composition prepared according to the process of claim 18.

* * * * *